(12) United States Patent
Farhadiroushan et al.

(10) Patent No.: US 10,145,821 B2
(45) Date of Patent: Dec. 4, 2018

(54) STRUCTURE MONITORING

(71) Applicants: Silixa Ltd., Hertfordshire (GB); Chevron USA Inc., San Ramon, CA (US)

(72) Inventors: Mahmoud Farhadiroushan, Hertfordshire (GB); Daniel Finfer, Hertfordshire (GB); Yousif Kamil, Hertfordshire (GB); Roy Lester Kutlik, San Ramon, CA (US)

(73) Assignees: Silixa Ltd., Elstree Hertfordshire (GB); Chevron USA Inc., San Ramon, CA (US)

( * ) Notice: Subject to any disclaimer, the term of this patent is extended or adjusted under 35 U.S.C. 154(b) by 0 days.

(21) Appl. No.: 13/944,469

(22) Filed: Jul. 17, 2013

(65) Prior Publication Data
US 2014/0022530 A1   Jan. 23, 2014

(30) Foreign Application Priority Data
Jul. 17, 2012   (GB) .................................. 1212701.5

(51) Int. Cl.
*G01N 29/24* (2006.01)
*G01S 5/18* (2006.01)
(Continued)

(52) U.S. Cl.
CPC ..... *G01N 29/2418* (2013.01); *E21B 47/0006* (2013.01); *E21B 47/091* (2013.01);
(Continued)

(58) Field of Classification Search
CPC ..... G01B 11/162; G01B 11/161; G01B 11/18; G01B 9/02095; G01B 11/16;
(Continued)

(56) References Cited

U.S. PATENT DOCUMENTS 4,342,907 A * 8/1982 Macedo ................. G01K 1/024
177/210 R
4,443,700 A * 4/1984 Macedo ................. G01B 11/18
250/227.16
(Continued)

FOREIGN PATENT DOCUMENTS

CN   1995935 A   7/2007
GB   1587712 A   4/1981
(Continued)

OTHER PUBLICATIONS http://en.wikipedia.org/wiki/Distributed_acoustic_sensing.*
(Continued)

*Primary Examiner* — Mohamed K Amara
(74) *Attorney, Agent, or Firm* — Osha Liang LLP

(57) ABSTRACT

A method and apparatus for monitoring a structure using an optical fiber based distributed acoustic sensor (DAS) extending along the length of the structure. The DAS is able to resolve a separate acoustic signal with a spatial resolution of 1 m along the length of the fibre, and hence is able to operate with an acoustic positioning system to determine the position of the riser with the same spatial resolution. In addition, the fiber can at the same time also detect much lower frequency mechanical vibrations in the riser, for example such as resonant mode vibrations induced by movement in the surrounding medium. By using vibration detection in combination with acoustic positioning then overall structure shape monitoring can be undertaken, which is useful for vortex induced vibration (VIV) visualisation, fatigue analysis, and a variety of other advanced purposes. The structure may be a sub-sea riser.

18 Claims, 19 Drawing Sheets

(51) Int. Cl.
| | |
|---|---|
| *E21B 47/00* | (2012.01) |
| *E21B 47/09* | (2012.01) |
| *G01H 9/00* | (2006.01) |
| *G01S 5/26* | (2006.01) |
| *G01S 5/30* | (2006.01) |
| *G01D 5/353* | (2006.01) |

(52) U.S. Cl.
CPC .............. *G01H 9/004* (2013.01); *G01S 5/18* (2013.01); *G01S 5/186* (2013.01); *G01S 5/26* (2013.01); *G01S 5/30* (2013.01); *G01D 5/35383* (2013.01)

(58) Field of Classification Search
CPC ....... G01B 11/2441; G01L 1/24; G01L 1/242; G01L 311/2441; G01D 5/35303; G01D 5/266; G01D 5/268; G01N 29/2418; G01N 29/12; G01N 29/46; G01N 21/1702; G01N 2291/0423; G01N 29/348; G01N 29/0681; G01J 9/02; G01J 2009/0226; G01H 9/00; G01H 9/004; G01H 13/00; G01H 9/006; A61B 5/0095; A61B 5/0059; A61B 5/1455
USPC ....... 356/35.5, 32, 477, 520, 480, 450, 73.1, 356/484; 73/800, 802; 385/12, 13; 250/227.14, 227.19
See application file for complete search history.

(56) References Cited

U.S. PATENT DOCUMENTS

| | | | | |
|---|---|---|---|---|
| 4,616,898 | A * | 10/1986 | Hicks, Jr. ............. | G02B 6/2821 359/327 |
| 5,602,327 | A * | 2/1997 | Torizuka ................ | H04R 17/00 73/40.5 A |
| 5,633,494 | A | 5/1997 | Danisch | |
| 5,946,429 | A | 8/1999 | Huang et al. | |
| 5,978,739 | A | 11/1999 | Stockton | |
| 6,055,391 | A * | 4/2000 | Jackson ............... | G01B 11/272 356/614 |
| 6,082,193 | A * | 7/2000 | Paulson ...................... | 73/152.58 |
| 6,256,090 | B1 | 7/2001 | Chen et al. | |
| 6,913,079 | B2 | 7/2005 | Tubel | |
| 7,751,977 | B2 * | 7/2010 | Winkler et al. .................... | 702/3 |
| 7,810,378 | B2 * | 10/2010 | Hunaidi et al. ............ | 73/40.5 A |
| 7,891,246 | B2 * | 2/2011 | Lander ................. | G01M 3/243 702/51 |
| 8,408,064 | B2 * | 4/2013 | Hartog et al. .................. | 73/643 |
| 8,699,009 | B2 * | 4/2014 | Li et al. ............................ | 356/33 |
| 8,924,158 | B2 * | 12/2014 | Kragh et al. ..................... | 702/17 |
| 9,322,702 | B2 * | 4/2016 | Lumens ................ | G01H 9/004 |
| 9,377,559 | B2 * | 6/2016 | Cooper ............... | G01V 11/002 |
| 9,453,821 | B2 * | 9/2016 | Minto ..................... | F17D 5/005 |
| 9,476,760 | B2 * | 10/2016 | Brady ...................... | G01V 1/40 |
| 9,612,189 | B2 * | 4/2017 | Hansen ................. | G01H 9/004 |
| 9,617,847 | B2 * | 4/2017 | Jaaskelainen ......... | E21B 47/123 |
| 2003/0075361 | A1 | 4/2003 | Terry et al. | |
| 2004/0201687 | A1 | 10/2004 | Perotti et al. | |
| 2006/0245469 | A1 | 11/2006 | Koeniger | |
| 2009/0009268 | A1 * | 1/2009 | Edmonson ........... | G01N 29/022 333/190 |
| 2009/0132183 | A1 * | 5/2009 | Hartog et al. .................. | 702/42 |
| 2010/0107754 | A1 | 5/2010 | Hartog et al. | |
| 2011/0069302 | A1 | 3/2011 | Hill et al. | |
| 2012/0020184 | A1 | 1/2012 | Wilson et al. | |
| 2012/0060615 | A1 | 3/2012 | Farhadiroushan et al. | |
| 2012/0078534 | A1 | 3/2012 | Selker et al. | |
| 2012/0092960 | A1 | 4/2012 | Gaston et al. | |
| 2012/0179390 | A1 | 7/2012 | Kimmiau et al. | |
| 2013/0208259 | A1 * | 8/2013 | Graham et al. | |
| 2015/0177126 | A1 * | 6/2015 | Tamayo De Miguel .................... | B82B 3/0085 73/643 |
| 2015/0338251 | A1 * | 11/2015 | van Neer ................ | G01L 1/246 600/424 |
| 2017/0010412 | A1 * | 1/2017 | Racosky ............... | C03C 25/106 |

FOREIGN PATENT DOCUMENTS

| | | | |
|---|---|---|---|
| GB | 2436142 A | 9/2007 | |
| GB | 2457278 A | 8/2009 | |
| JP | 4254689 B2 | 4/2009 | |
| WO | 02063332 A1 | 8/2002 | |
| WO | WO 03100453 A1 * | 12/2003 | .............. G01S 11/14 |
| WO | 2009/148824 A1 | 12/2009 | |
| WO | 2010/034986 A1 | 4/2010 | |
| WO | 2010136810 A2 | 12/2010 | |
| WO | 2012/018460 A2 | 2/2012 | |
| WO | 2012059108 A1 | 5/2012 | |
| WO | 2012063066 A2 | 5/2012 | |
| WO | 2013/093478 A1 | 6/2013 | |

OTHER PUBLICATIONS https://en.wikipedia.org/wiki/Nyquist%E2%80%93Shannon_sampling_theorem.*
http://philschatz.com/physics-book/contents/m42249.html (May 2012).*
Combined Search and Examination Report dated Mar. 209, 2014 in corresponding application No. GB1402175.2 (7 pages).
Fistas N. & Manikas, A. (1994). "A New General Global Array Calibration Method"; ICASSP Proceedings (pp. 73-76) IEEE (4 pages).
Kamil, Y. (2011) "Localisation and tracking in arrayed wireless sensor networks"; London: Theis (PhD), Department of Electrical and Electronic Engineering, Imperial College London (266 pages).
Kutlik, R. & Allen, J. (1998); "Flow Assurance Instrumentation"; Offshore Technology Conference, 8733-MS (6 pages).
Mellen, R.N. (1952) "Thermal-noise limit in the detection of underwater acoustic signals"; Journal of the Acoustical Society of America, 24, 478 (3 pages)
Thorp. W. H. (1966); "Analytic Description of the low frequency sound attenuation in the Deep Ocean"; Journal of the Acoustical Society of America, 39 (904) (1 page)
Urick, R. J. (1984); "Ambient noise in the Sea"; Department of hte Navy (US), Naval Sea Systems Command. 20070117128 (194 pages).
Search Report dated Jan. 7, 2013 in corresponding United Kingdom application No. GB1212701.5 (1 page).
Further Search Report dated Feb. 22, 2013 in corresponding United Kingdom application No. GB1212701.5 (1 page).
Combined Search and Examination Report dated Jan. 13, 2014 in corresponding Great Britian application No. GB1312718.8 (7 pages).
International Search Report and Written Opinion dated Feb. 7, 2014 in corresponding international application No. PCT/GB2013/051903 (15 pages).
Communication Relating to the Results of the Partial International Search issued in corresponding International Application No. PCT/GB2013/051903 (3 pages).
Examination Report issued in corresponding British Application No. GB1312718.8; dated Feb. 4, 2015 (5 pages).
Examination Report issued in corresponding British Application No. GB1402175.2; dated Apr. 14, 2015 (3 pages).
Patent Examination Report No. 1 dated Oct. 27, 2016 in corresponding Australian application No. 2013291747 (4 pages).
Office Action dated Nov. 30, 2016 in related U.S. Appl. No. 13/944,407.
*Electric Power Group v. Alstom*; U.S. Court of Appeals for the Federal Circuit; decided Aug. 1, 2016.

* cited by examiner

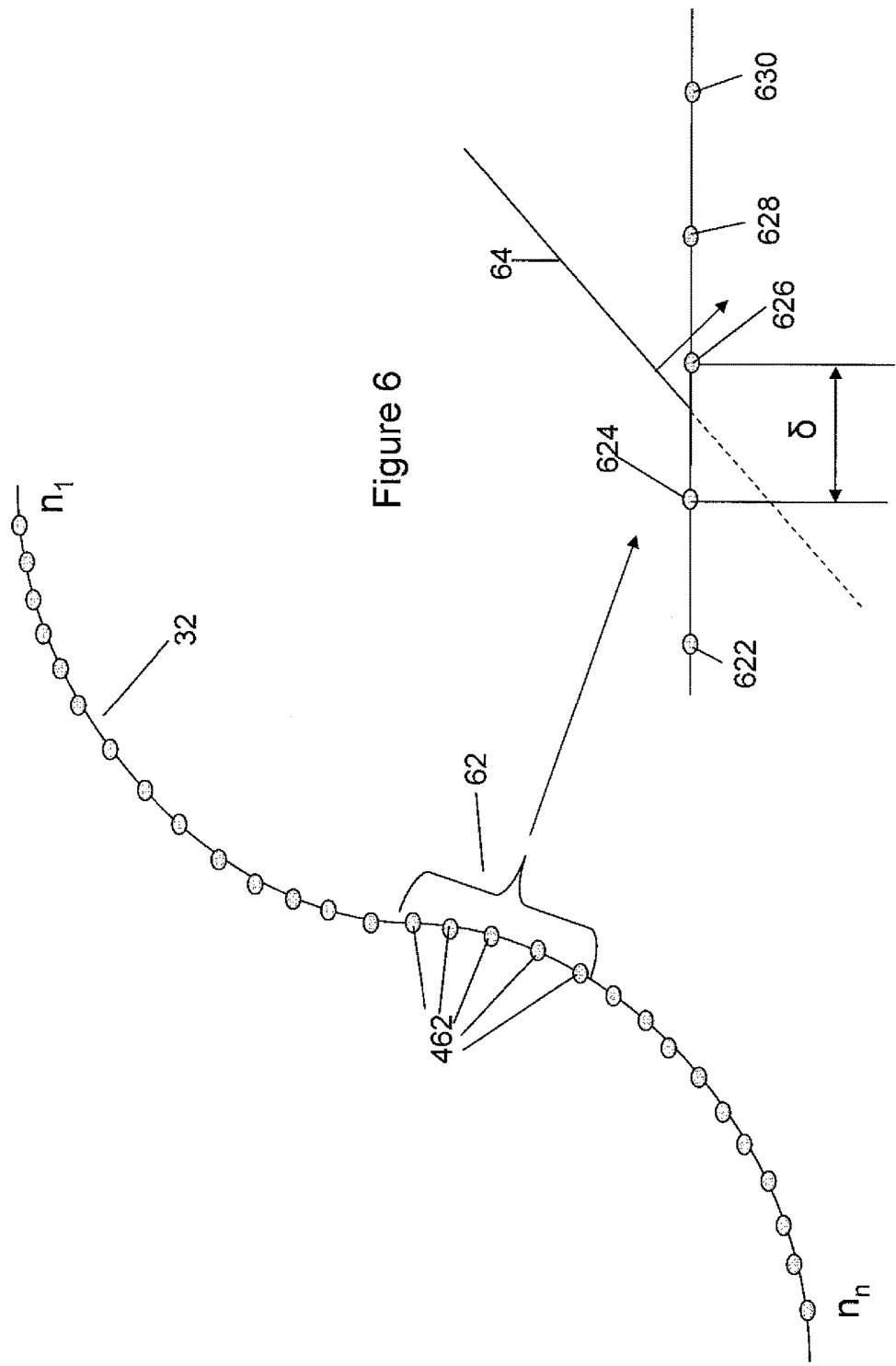

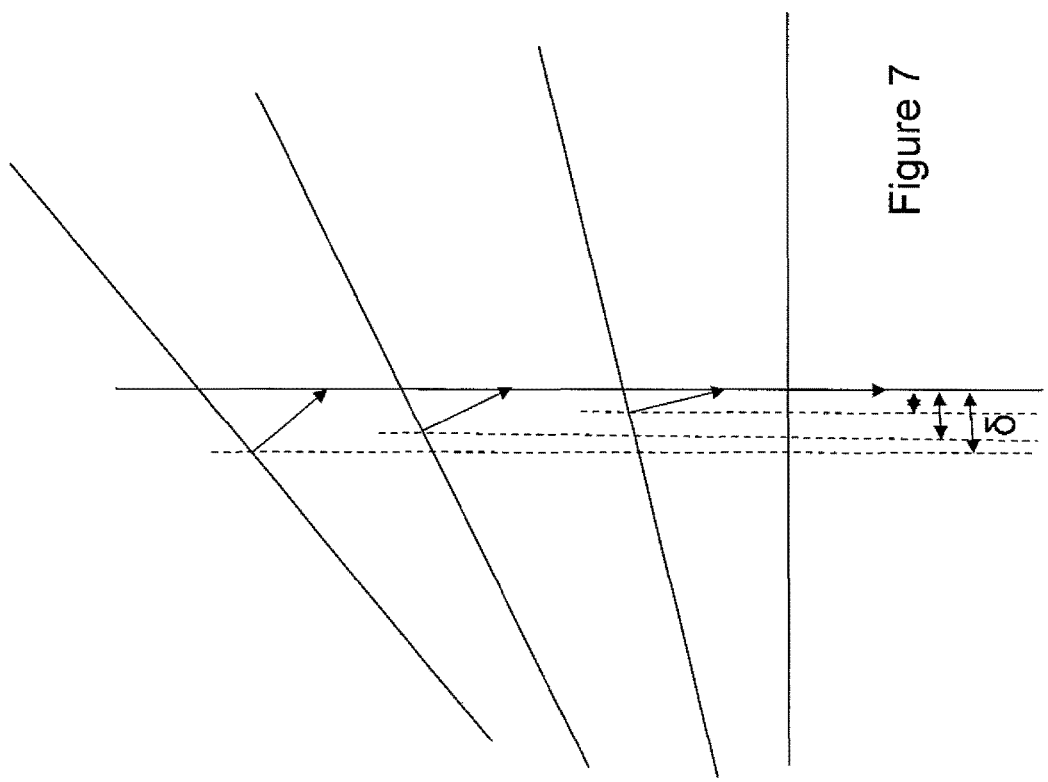

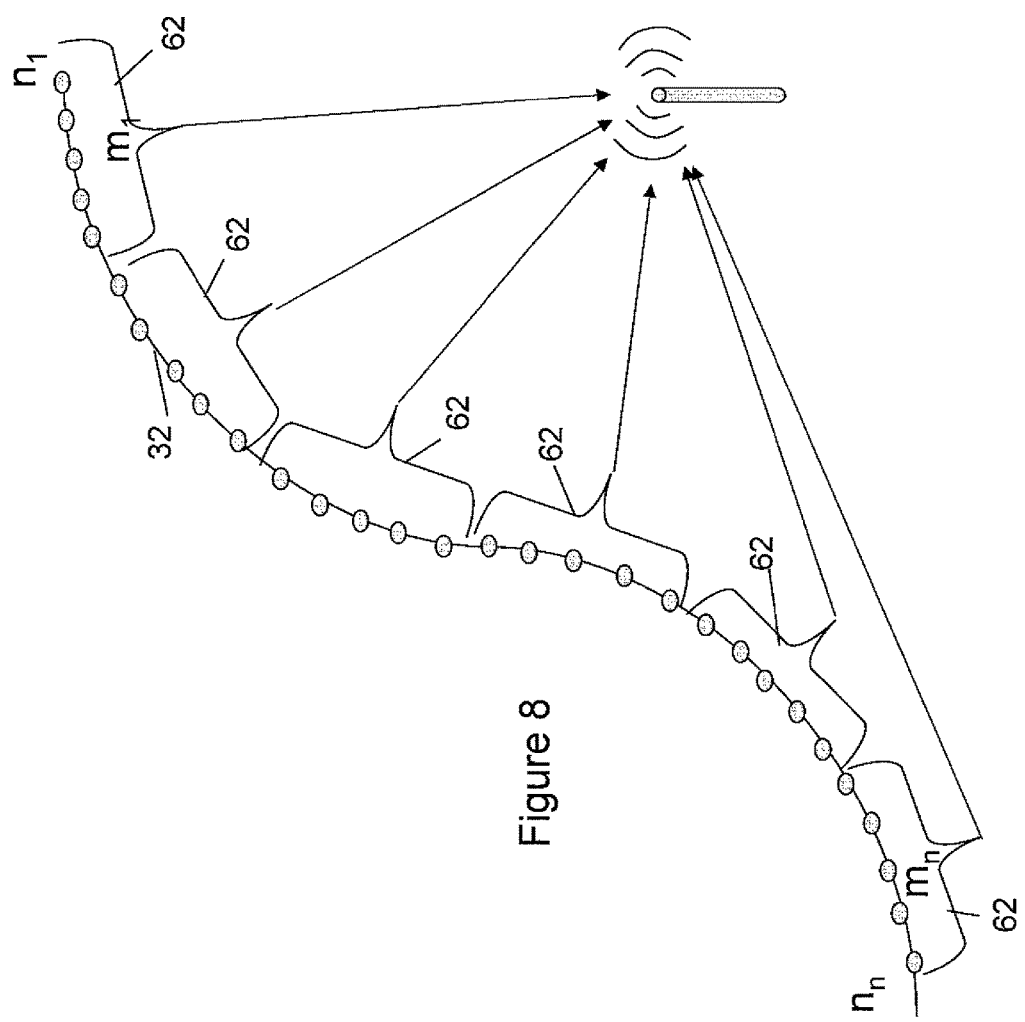

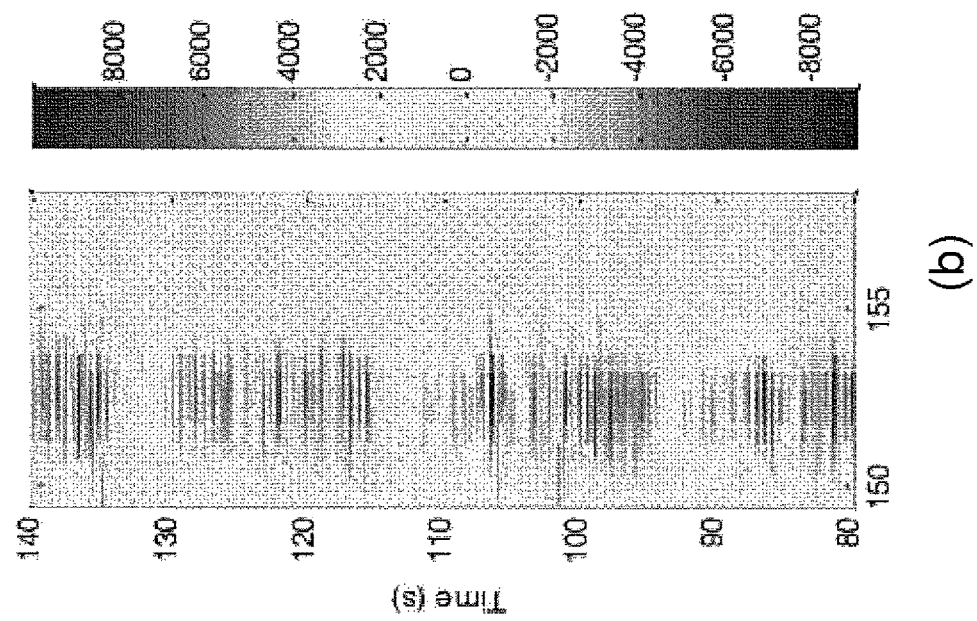
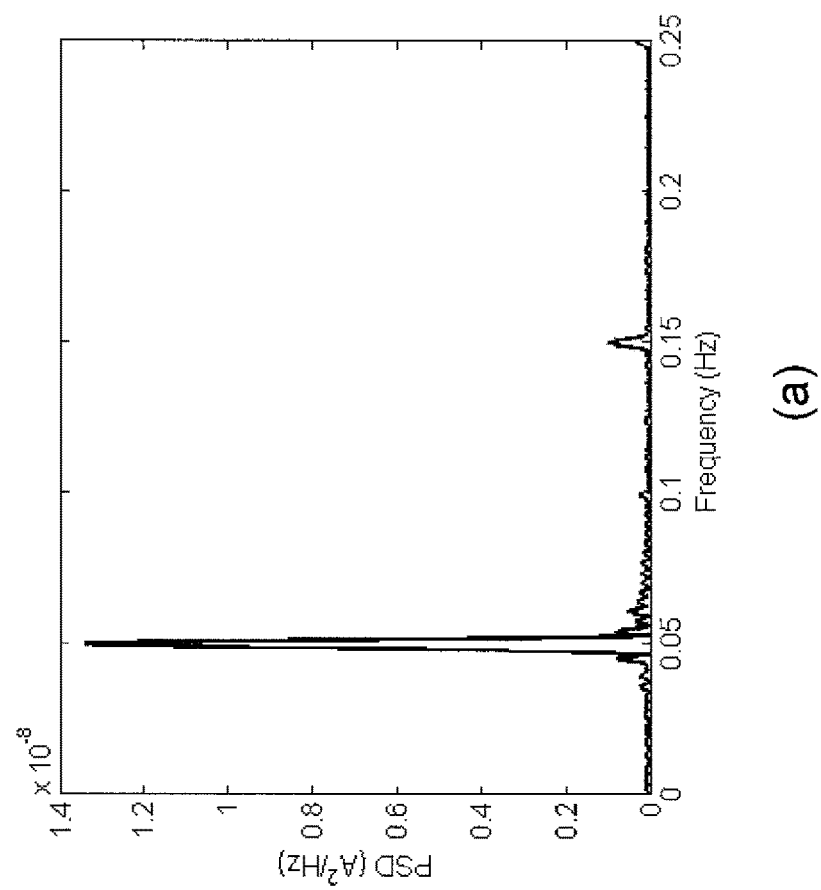
Figure 17

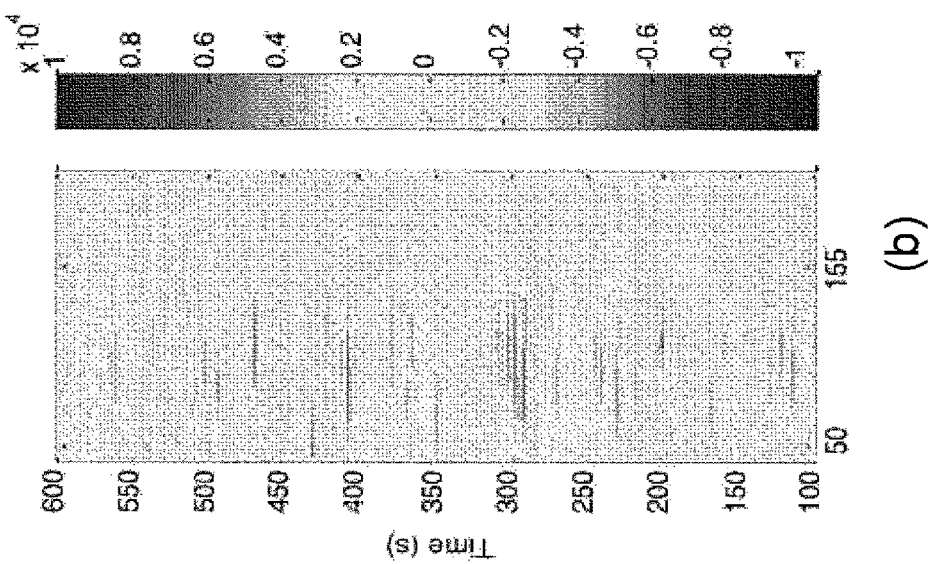
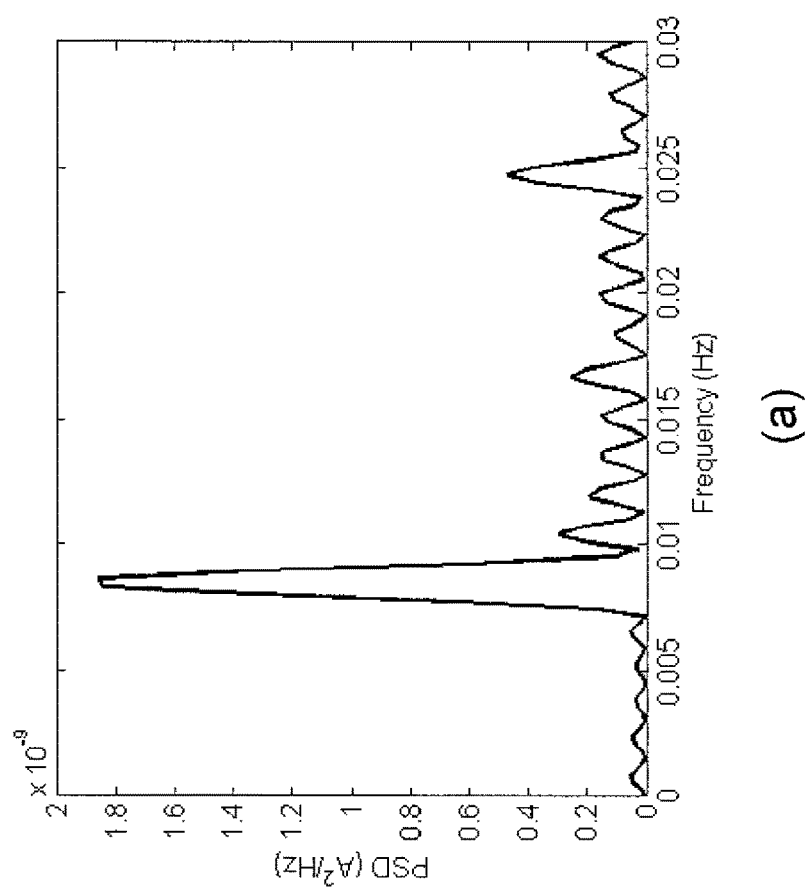
Figure 18

STRUCTURE MONITORING

TECHNICAL FIELD

The present invention relates to the monitoring of structures such as, for example, sub-sea risers, and particularly to a method and apparatus for monitoring structures using an optical fiber distributed acoustic sensor (DAS) capable of detecting sound at short intervals along the length of the structure. In one embodiment the DAS system is employed as part of an acoustic positioning system to help determine the shape of the structure along its length. In another embodiment the DAS system is employed to monitor mechanical vibration of the structure itself. In a preferred embodiment both vibration monitoring and acoustic positioning are undertaken by the same DAS equipment.

BACKGROUND TO THE INVENTION AND PRIOR ART

Sub-sea risers are used to transport materials between the seafloor and the surface (and vice versa), and are used extensively in the oil and gas industries. They come in several different variants, and are used for many purposes, particularly the transport of produced hydrocarbons, as well as production materials, such as injection fluids, control fluids and gas lift. Risers may be rigid or flexible, and variants include attached risers, pull tube risers, steel catenary risers, top-tensioned risers, riser towers and flexible riser configurations, as well as drilling risers.

Chevron originally proposed the concept of tracking strategic points on a riser, mooring lines, or other dynamic subsea structures via active hydro-acoustics in the 1990's (Kutlik, R., & Allen, J. (1998). Flow Assurance Instrumentation. *Offshore Technology Conference*, 8733-MS). However, the length of many risers means that for proper tracking many individual hydrophones are required along the length of the riser, which heretofore has been prohibitively expensive.

In addition to the above, acoustic positioning systems are also known in the art. One known type of acoustic positioning system is known as a "long-baseline" system. Here, acoustic sources of known location emit characteristic sonar pings, usually in response to a ping received from a device the location of which is to be determined. The sonar on the device detects the pings, and based on the time elapsed between its own ping and receiving the ping from the known source in reply, together with measurements of the speed of sound given present water conditions, the device is able to calculate its distance from the source. By calculating the distance to several different known sources and triangulating the results, the position of the device relative to the known positions of the sources can be determined. The technique is substantially identical to that used in GPS systems. To determine relative location in 3 dimensions, distance to at least four known sources is required.

Thus, both acoustic positioning and the concept of the monitoring of subsea risers using active hydro acoustics are known in theory, but heretofore no successful deployment of such a system has taken place. As noted above, the number of hydrophones required to properly monitor a subsea riser has been prohibitive, and there are challenging deployment issues.

WO 2012/018460 describes how a distributed optical acoustic sensor can be used in combination with acoustic pingers that are part of a survey spread for positioning of one or more objects of interest in relation to a structure carrying the distributed optical acoustic sensor. Such objects may include a streamer towed through a body of water, or a seabed cable positioned on the sea floor. Alternatively marine vessels, or fish or marine mammals may also be positioned.

In addition, the applicant's earlier application WO 2010/136810 describes an application of a distributed optical acoustic sensor to dynamic positioning of a riser. Here an optical fibre sensor measures the time of flight of acoustic signals received at different locations along the riser, and thereby determines the position of the riser.

Therefore, whilst positioning per se using optical fibre acoustic sensors has been suggested in the prior art, there is still no solution which allows for proper monitoring of a riser or other structure along its whole length, and which particularly allows for fatigue analysis, for example, to take place.

SUMMARY OF THE INVENTION

The present invention addresses the above noted deficiencies of the prior art by providing a method and apparatus for monitoring a structure such as a subsea riser using an optical fibre based distributed acoustic sensor (DAS) extending along the length of the structure. The DAS is able to resolve a separate acoustic signal with a spatial resolution of 1 m along the length of the fibre, and hence is able to operate with an acoustic positioning system to determine the shape of the structure with the same spatial resolution. In addition, the fiber can at the same time also detect much lower frequency mechanical vibrations in the structure, for example such as resonant mode vibrations induced by movement in the surrounding medium. By using vibration detection in combination with acoustic positioning then overall structure shape monitoring can be undertaken, which is useful for vortex induced vibration (VIV) visualisation, fatigue analysis, and a variety of other advanced purposes.

In view of the above, from one aspect an embodiment of the invention provides a method of monitoring the position of a structure using an optical fiber distributed acoustic sensor deployed in a known relationship with respect to the structure such that a known part of the optical fiber corresponds to a known part of the structure. The method may comprise using the optical fiber as a distributed acoustic sensor to detect, at a plurality of acoustic sensor positions along the fibre, acoustic signals emitted by a plurality of acoustic sources deployed at known positions in an area in which the structure to be monitored is located. Relative positions of a plurality of the acoustic sensors with respect to the acoustic sources are then calculated in dependence on the detected acoustic signals from the acoustic sources. From the calculated positions of the sensors along the fibre, a shape, or shape and position, of the structure can then be determined in further dependence on the known relationship between the fiber and the structure.

With the above the shape and position of a structure such as a sub-sea riser can be monitored in a convenient manner. In this respect, sub sea risers often have fiber optic cables passing through them, which may be used as the fiber optic cable of the DAS system. Moreover, such fiber optic DAS systems can resolve acoustic signals with a spatial resolution of better than 1m, and hence high spatial resolution monitoring of the structure position and movement can be obtained. This allows for advanced fatigue monitoring and logging, and other such analysis, to take place.

In a preferred embodiment determining the shape, or shape and position, of the structure is repeatedly performed so as to track changes in shape and/or movement of the structure with respect to time. As noted above, this allows for further monitoring and/or analysis of the structure, such as fatigue monitoring, to be undertaken in dependence on the tracked changes in shape and/or movement of the structure.

In one embodiment the relative position of one of the acoustic sensors on the fiber is determined in dependence upon the relative position determined for one or more others of the sensors. Hence, a priori knowledge of the fact that the acoustic sensors are positioned along an optical fiber in a known relationship can be used to improve the positioning (and hence shape) that is calculated. Specifically, in one embodiment the relative position found for one of the acoustic sensors on the fiber is checked to determine whether it is within an allowable distance of the position previously found for another of the acoustic sensors on the fiber, given the known length of fiber between the respective positions of the two acoustic sensors on the fiber. If the calculated position is not within the allowable distance, then one or other of the positions is incorrect, and should be recalculated.

In some embodiments the relative position of one of the sensors is determined in dependence on the time taken for respective signals from one or more of the acoustic sources of known position to reach the sensor. In this respect, the positioning system operates very much like the well known GPS system, except using acoustic signal such as sonar signals. In this respect, to solve for an unknown position in three dimensions requires signals to be received from at least four known acoustic sources, and the calculation involves finding the distance to each of the sources.

However, in a preferred embodiment the calculating further comprises forming a plurality of subsets of the acoustic sensors, a subset of sensors comprising a virtual line array of acoustic sensors. A direction from a subset of sensors to an acoustic source of known position may then be determined in dependence on a phase delay of receipt of an acoustic signal from the acoustic source across the acoustic sensors of the array. By finding direction to a source rather than distance to a source then the number of sources required for a position fix is reduced. Specifically, in one embodiment the position of a subset may be determined by detecting direction to n acoustic sources, where there are n degrees of freedom of movement of the sensors forming the subset.

In some embodiments the subsets of sensors may be contiguous along the fiber, whereas in other embodiments the subsets of sensors may overlap, such that any one acoustic sensor is a member of more than one subset. In this latter case, more positions of points along the fiber can be obtained, and hence spatial resolution is increased.

From another aspect an embodiment of the present invention provides a method of vibration detection in a structure using an optical fiber distributed acoustic sensor deployed in a known relationship with respect to the structure such that a known part of the optical fiber corresponds to and moves with a known part of the structure. The method in particular may comprise detecting backscattered light on the fiber, the backscattered light being dependent on strain induced in the fibre due to mechanical strain in the structure to which the fiber relates caused by vibrations in the structure. Then, from the detected backscatter, a signal representative thereof is processed to determine a frequency of oscillation of the vibrations in the structure. The backscattered light may be Rayleigh and/or Brillouin light generated along an optical fibre.

With the above, an optical fiber based DAS can also be used to detect mechanical vibrations in a structure, for example vortex induced vibrations.

In a preferred embodiment the same optical fiber distributed acoustic sensor system is used to perform both vibration detection in accordance with the above aspect, and position detection in accordance with the first aspect. No additional sensor system is therefore required in order to perform both functions. In this respect, within a preferred embodiment frequency filtering of the signal detected by the optical fibre DAS is undertaken to divide the signal into low frequencies and high frequencies, wherein the low frequencies (<100 Hz) are used for vibration detection, and the high frequencies (>1 kHz) are used for position and/or shape monitoring.

In addition, in further embodiments the optical fiber DAS may also undertake passive acoustic monitoring. Such passive acoustic monitoring may comprise detecting acoustic events having an energy greater than a predetermined energy threshold, and hence be used to try and detect catastrophic failures, or cracking of the structure.

In preferred embodiments the structure is a subsea riser, or other subsea structure such as a cable or mooring line.

The signal processing performed to obtain the acoustic output, and detect position or vibration is usually performed in software by a processor which receives a data signal corresponding to or derived from backscattered light from along the fibre. In a further aspect, therefore, there is provided a computer program or suite of computer programs so arranged such that when executed by a computer they cause the computer to operate in accordance with the method of any of the above aspects. Also provided is a computer readable storage medium storing a computer program or at least one of the suite of computer programs.

From another aspect of the invention an embodiment provides a system for monitoring the position of a structure. The system includes an optical fiber distributed acoustic sensor system deployed in a known relationship with respect to the structure such that a known part of the optical fiber corresponds to a known part of the structure. The sensor system further comprises a processor arranged to use the optical fiber as a distributed acoustic sensor to detect, at a plurality of acoustic sensor positions along the fibre, acoustic signals emitted by a plurality of acoustic sources deployed at known positions in an area in which the structure to be monitored is located The processor then calculates relative positions of a plurality of the acoustic sensors in dependence on the detected acoustic signals from the acoustic sources; and from the calculated positions of the sensors along the fibre is then able to further determine a shape, or shape and position, of the structure in dependence on the known relationship between the fiber and the structure.

Yet another aspect of the invention provides embodiments that detect vibration in a structure. Such systems comprise an optical fiber distributed acoustic sensor system deployed in a known relationship with respect to the structure such that a known part of the optical fiber corresponds to and moves with a known part of the structure. The sensor system further comprises an interferometer arrangement arranged to detect backscattered light on the fiber, the backscattered light being dependent on strain induced in the fibre due to mechanical strain in the structure to which the fibre relates caused by vibrations in the structure. A processor in the sensor system is then further arranged, from the detected backscatter, to process a signal representative thereof to determine a frequency of oscillation of the vibrations in the structure. The backscattered light may be Rayleigh or Brillouin backscatter.

In a preferred embodiment, the same optical fiber distributed acoustic sensing system is able to perform both position monitoring and vibration detection at the same time, using the same backscattered signal from the fibre.

Further features and advantages will be apparent from the appended claims.

BRIEF DESCRIPTION OF THE DRAWINGS

Further features and advantages of the present invention will become apparent from the following description of an embodiment thereof, presented by way of example only, and by reference to the drawings, wherein like reference numerals refer to like parts, and wherein:

FIG. 6 is a diagram illustrating how subsets of acoustic sensors can form virtual line arrays;

FIG. 7 is a diagram illustrating hoe phase delay along a line array varies with angle of incidence of an acoustic wave;

FIGS. 8 and 9 are diagrams illustrating the operation of different variants of a third embodiment;

FIGS. 16, 17, and 18 are graphs and other data showing the output of a DAS at different respective frequencies of oscillation of the experimental rig;

DESCRIPTION OF THE EMBODIMENTS

Overview of embodiments

A brief overview of embodiments will first be given, followed by description of specific embodiments. Embodiments of the invention fall into three classes, a first class relating to embodiments which perform structure position and shape determination using an acoustic positioning system, a second class relating to mechanical vibration detection in the structure, possibly as resonant modes, and a third class which combine the position and shape determination and the vibration detection into the same embodiment. Within the described embodiments the structure being monitored is a subsea riser, and in preferred embodiments this is the case. However, in other embodiments the structure may be any other structure or structure type, such as buildings, towers, chimneys, pylons, antennas, process plant, or any other structure.

Figure 1:
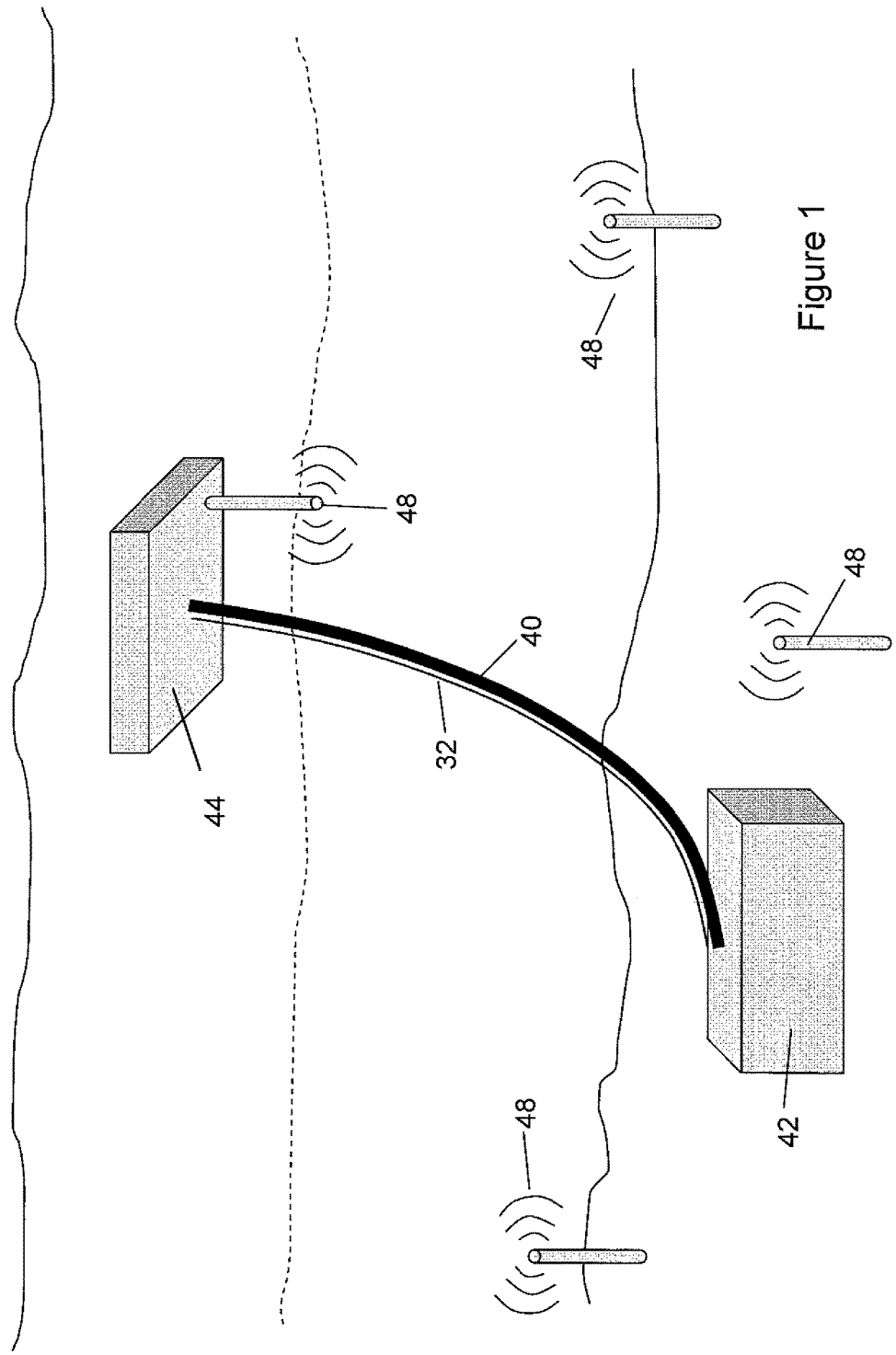
FIG. 1 is a diagram illustrating an operating environment of embodiments of the invention.

FIG. 1 shows a typical riser deployment used in an embodiment of the invention. Here, a riser 40 extends from a seafloor installation 42 such as a well top, production facility or blow-out preventer to a surface facility such as a ship or rig 44. Substantially co-located with and extending along the length of the riser is an optical fiber cable 32. The cable 32 may be clamped to the outside of the riser, or in other embodiments may be contained within the riser, or may alternatively be spiralled around the outer surface of the riser. Whichever configuration is adopted, there is a known relationship between any particular part of the optical fiber and a corresponding part of the riser, in that it is known which part of the optical fiber is adjacent or connected to which part of the riser.

Also provided are a number of acoustic positioning system acoustic sources 48, which are each at a known location and each emit respectively identifiable acoustic signals, either continuously or repeatedly.

The optical fiber cable acts as a distributed acoustic sensor. Distributed optical fiber sensors operate by launching a pulse of light into an optical fiber. This generates weak scattered light which is captured by the fiber and carried back towards the source. By timing the return of this backscattered light, it is possible to accurately determine the source of the backscatter and thereby sense at all points along a fiber many tens of kilometers in length. Three different physical mechanisms produce the backscatter, being Rayleigh, Brillouin and Raman scattering. A common instrument that uses the intensity of the backscattered Rayleigh light to determine the optical loss along the fiber is known as an Optical Time Domain Reflectometer (OTDR). Rayleigh backscatter light is also used for coarse event/vibration sensing. Raman light is used by a Distributed Temperature Sensor (DTS) to measure temperature, achieving a temperature resolution of <0.01° C. and ranges of 30 km+. However the response time of distributed temperature sensors is typically a few seconds to several minutes. Distributed Brillouin based sensors have been used to measure strain and temperature and can achieve faster measurement times of 0.1 second to a few seconds with a resolution of around 10 microstrain and 0.5° C.

Figure 2:
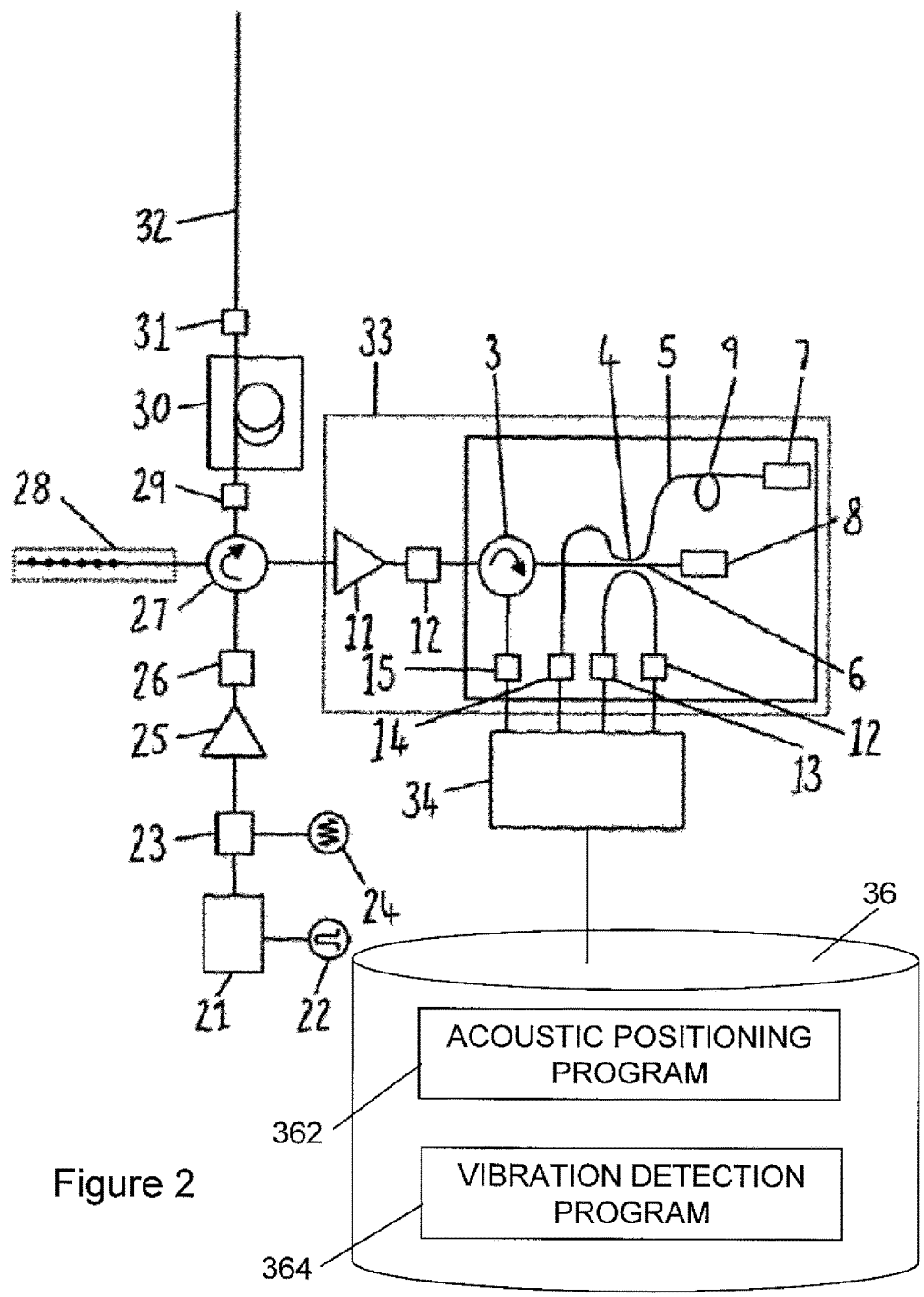
FIG. 2 is a diagram of an interferometer apparatus used in embodiments of the invention.

In order to provide for acoustic sensing via the optical fiber in a particular embodiment of the invention, described here in order to provide an example of a preferred implementation of embodiments of the present invention, the optical fiber 32 is coupled to an interferometer such as illustrated in FIG. 2, located for example in the surface vessel 44.

With reference to FIG. 2, light emitted by a laser (21) is modulated by a pulse signal (22). An optical amplifier (25) is used to boost the pulsed laser light, and this is followed by a band-pass filter (26) to filter out the ASE noise of the amplifier. The optical signal is then sent to an optical circulator (27). An additional optical filter (28) may be used at one port of the circulator (27). The light is sent to sensing fiber (32), which is for example a single mode fiber or a multimode fibre. A length of the fiber may be isolated and used as a reference section (30), for example in a "quiet"

location or with a controlled reference signal. The reference section (30) may be formed between reflectors or a combination of beam splitters and reflectors (29) and (31). The reflected and the backscattered light generated along the sensing fiber (32) is directed through the circulator (27) and into the interferometer (33).

Within the interferometer, the incoming light is amplified in an optical amplifier (1), and transmitted to the optical filter (2). The filter (2) filters the out of band Amplified Spontaneous Emission noise (ASE) of the amplifier (1). The light then enters into an optical circulator (3) which is connected to a 3×3 optical coupler (4). A portion of the light is directed to the photodetector (12) to monitor the light intensity of the input light. The other portions of light are directed along first and second optical paths (5) and (6), with a path length difference between the two paths. Faraday-rotator mirrors (FRMs) (7) and (8) reflect the light back through the first and second paths (5) and (6), respectively. The Faraday rotator mirrors provide self-polarisation compensation along optical paths (5) and (6) such that the two portions of light efficiently interfere at each of the 3×3 coupler (4) ports. The optical coupler (4) introduces relative phase shifts of 0 degrees, +120 degrees and −120 degrees to the interference signal, such that first, second and third interference signal components are produced, each at a different relative phase.

First and second interference signal components are directed by the optical coupler (4) to photodetectors (13) and (14), and the third interference signal component incident on the optical circulator (3) is directed towards photodetector (15).

The photodetectors (12), (13), (14) and (15) convert the light into electrical signals. The electrical signals are digitised and then the relative optical phase modulation along the reference fiber (30) and the sensing fiber (32) is computed using a fast processor unit (34). The processor unit is time synchronised with the pulse signal (22). The path length difference between path (5) and path (6) defines the spatial resolution.

Methods for calculating the relative phase and amplitude from three phase shifted components of an interference signal are known from the literature. For example, Zhiqiang Zhao et al. ("Improved Demodulation Scheme for Fiber Optic Interferometers Using an Asymmetric 3×3 Coupler", J. Lightwave Technology, Vol.13, No.11, November 1997, pp. 2059-2068) and Huang et al (U.S. Pat. No. 5,946,429) describe techniques for demodulating the outputs of 3×3 couplers in continuous wave multiplexing applications.

The phase angle data is sensitive to acoustic perturbations experienced by the sensing fiber 32. As an acoustic wave passes through the optical fibre, it causes the glass structure to contract and expand. This varies the optical path length between the backscattered light reflected from two locations in the fiber (i.e. the light propagating down the two paths in the interferometer), which is measured in the interferometer as a relative phase change. In this way, the optical phase angle data can be processed to measure the acoustic signal at the point at which the light is reflected.

An example system corresponding to the above and that is commercially available is the Silixa iDAS system, available from Silixa Ltd, Elstree, London, United Kingdom. The Silixa iDAS system uses the above described interferometer arrangement to accurately and rapidly measure the Rayleigh backscattered signal with a precision and speed that allows acoustic measurements. The iDAS is so sensitive that it allows digital recording of acoustic fields at every location along an optical fiber with a frequency of up to 100 kHz.

In addition, by using digital signal processing, the acoustic response along the fiber can be combined to enhance the detection sensitivity by two-orders of magnitude, thereby exceeding the sensitivity of point sensors as well achieving highly directional information. With the DAS, the fiber acts as an acoustic antenna whose sensitivity and frequency response can be adjusted electronically by using different sensing configurations. For example, the fiber can be deployed in linear, directional or multi-dimensional array configurations. In addition, the precision that the DAS can achieve uniquely allows the speed of sound in the material surrounding the fiber to be accurately determined. This allows the DAS to detect, for example, the presence of gas in oil (a necessary step towards multiphase flow measurement).

In addition, further processing can be performed by processor 34 on the determined acoustic signal, for example to determine position information or to detect mechanical vibrations in the structure to which the fiber is attached. Therefore, as also shown in FIG. 2 and pertinent to the present embodiments, also provided as part of the apparatus of an embodiment is a computer readable medium 36 such as a flash drive or hard disk, which stores an acoustic positioning program 362 and a vibration detection program 364. As will be described later, the acoustic positioning program 362 is arranged to control the processor 34 to process the determined acoustic data from the optical fiber DAS to determine the position of the fiber, based on received acoustic signals from known acoustic sources 48. In addition, the vibration detection program 362 is arranged to control the processor 34 to process the determined acoustic data to look at significantly lower frequencies, and specifically to detect low frequency resonant vibrations of the riser structure, such as vortex induced vibrations. Such vibrations may not make actual acoustic noise, but are detectable by the DAS using the same physical mechanism of Rayleigh backscatter because as the fiber moves back and forth with the riser structure under the resonant vibration then parts of the fiber are placed under strain in the same manner as if they were within a vibro acoustic field. As such, the resonant vibration manifests itself in the DAS output in the same way as an acoustic input to the sensor array, although at a significantly lower frequency. Further details of the vibration detection performed by embodiments of the invention will be given later.

Hence, as described above, using a DAS such as that described turns a standard single mode fiber optic cable into a transduction system which functions like a string of hydrophones. The length and sensing density of this virtual string of hydrophones is limited by a combination of factors, including the sampling frequency and spatial resolution. For the sake of the discussion here, a 10 km fiber can be monitored using a Silixa iDAS with a sampling frequency of 10 kHz and a spatial resolution of about 1 m. Thus a single iDAS box can be used with a standard optical fiber to give the equivalent output of 10,000 hydrophones.

Acoustic positioning technology has been in wide use throughout the oil and gas industry for several decades. Positioning systems function by observing the signal from one or several controlled sources, and observing either changes in relative phase or absolute time-of-flight to determine the position of a receiver. This concept is unchanged regardless of the medium of interest and the radiation used to power the system. Thus an acoustic positioning can be conceptually similar to a GPS system in some implementations.

Given the capability of the DAS described above to turn a fiber into an array of virtual hydrophones, it is possible to consider a fiber as a string of discretely spaced sensors. The output from each of these sensors can then be manipulated just as one might for a standard sensor. In the case of a positioning system, this may involve observing the signal from a controlled receiver to find the position of that receiver, based, for example, on the receiver receiving signals from acoustic sources of known position. By doing this for each discrete acoustic zone along the fiber, one can extract the position of each zone and hence interpolate for the shape. If the position of each zone of the fiber is then related to the position of each zone of another structure, such as a riser, in a known way (for example by being co-located and fixed thereto), then knowing the shape of the fiber also gives us information of the shape of the structure, such as a riser, to which it is related.

In summary then, using an optical interferometer based DAS embodiments of the invention are able to measure acoustic signals at approximately 1 m resolution along the length of an optical fiber attached to a subsea structure, such as a riser. Combined with an acoustic positioning system such as a long baseline system then the position of each segment of the fiber may be determined, and hence also the related position of the structure. This therefore allows for shape monitoring of the structure such as riser to be undertaken, by interpolating between the found positions, and knowing the spatial relationship between the fiber and the structure. Changes in the shape or shape and position of the structure with respect to time may also be monitored, to determine how the structure moves under various conditions, such as loading conditions, or with movement of the surrounding environment (such as flows or vortices in the surrounding water, in the case of a riser). In addition, and advantageously, the fiber is also able to detect resonant vibrations of the structure, which occur at much lower, and generally inaudible, frequencies, due to the expansion and compression of the structure under the vibration being transferred to the fiber, and hence inducing strain in the fiber which affects the backscatter in a similar manner to being placed in a vibro acoustic field.

In view of the above overview, several embodiments of the invention will now be described.

Acoustic Positioning System for Shape Determination

Figure 3:
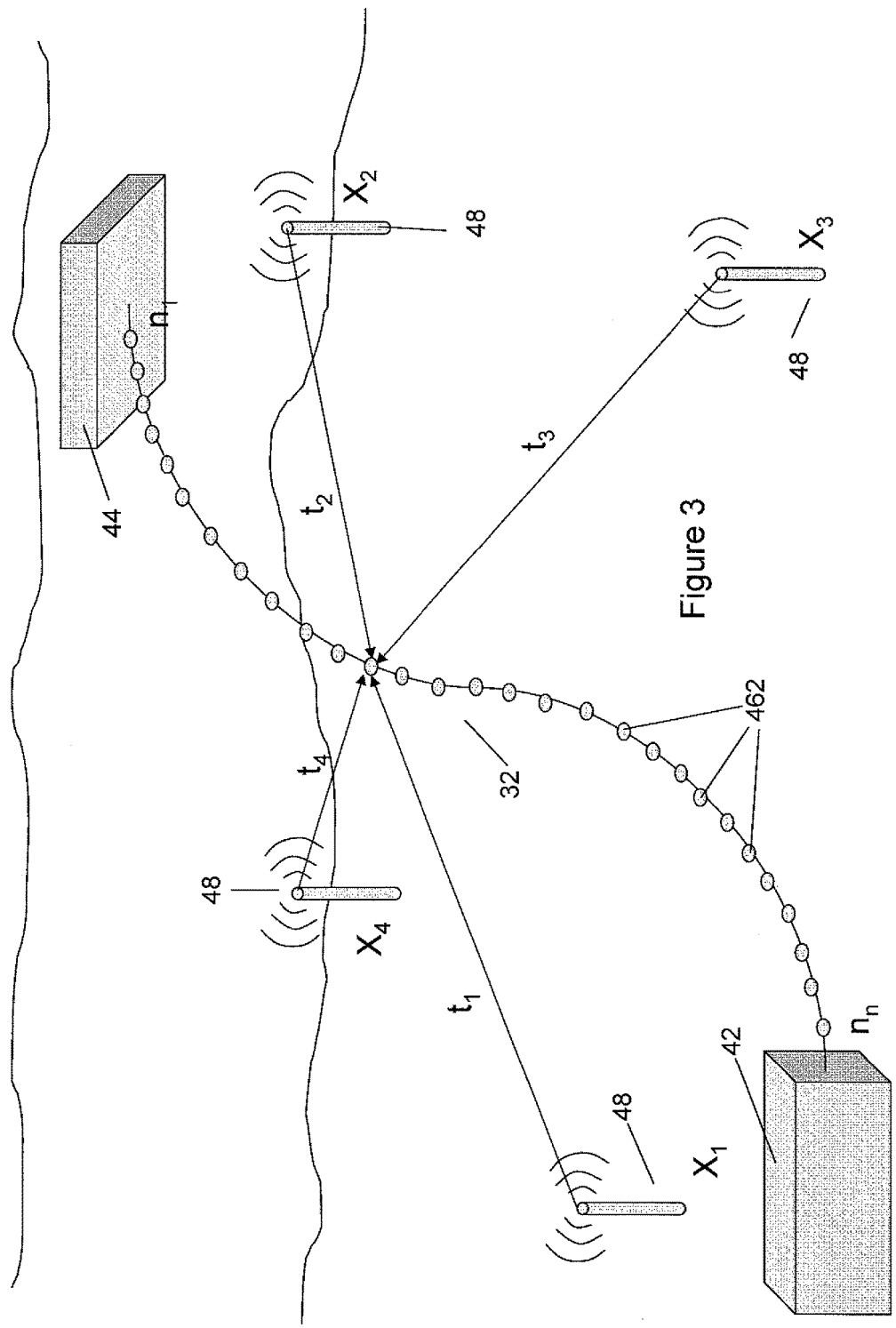
FIG. 3 is a diagram illustrating an operating environment of embodiments of the invention.

FIG. 3 illustrates the operating environment of a first embodiment. Here, fiber 32 attached to or otherwise related in a known manner to a subsea riser (not shown) extends from surface vessel 44 to seafloor installation 42. The fiber 32 forms part of a DAS, as described above, that is able to sense an incident vibro acoustic field with a spatial resolution of approximately 1 m. Hence, an acoustic sensor 462 is formed approximately every 1 m along fiber 32, to give n acoustic sensors along the length of fiber 32.

Also provided are x acoustic sources Xn (48), with four such sources being shown in FIG. 3. Each acoustic source is at a known location, and emits an identifiable acoustic signal, for example at a specific, known, frequency, or of a particular pattern.

Figure 4:
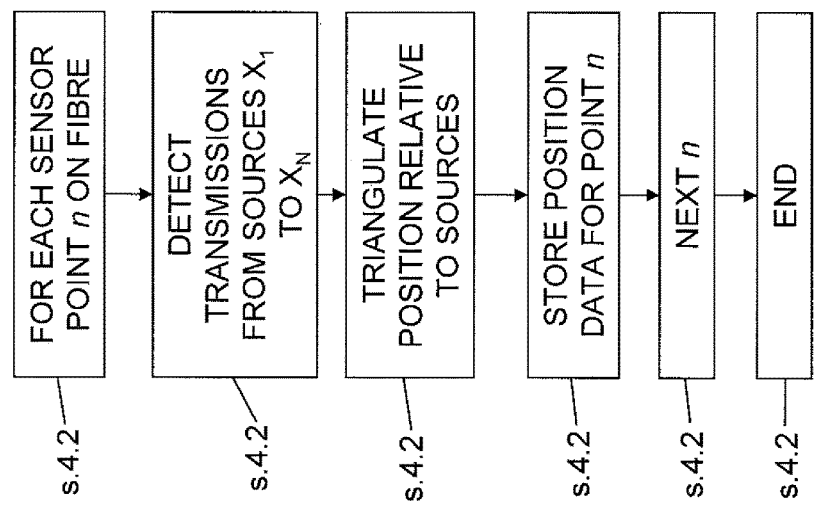
FIG. 4 is a flow diagram of a first embodiment.

In a first embodiment of the invention, each sensor 462 is treated individually, and a respective location found for a particular sensor without reference to positions found for other sensors on the fibre. FIG. 4 illustrates the steps involved.

With reference to FIG. 4, when running acoustic positioning program 362 processor 34 acts to determine a position for each sensor 462 on the fibre, as noted, by initiating a FOR processing loop, at s.4.2. Within the loop for a particular sensor at s.4.4 the acoustic transmissions from the acoustic sources Xn (48) are respectively detected, and respective time of flight for each transmission found, to give a set of time data tn. The time of flight for each acoustic signal can then be converted, by knowing the local speed of sound in water, into a distance from each sensor 462 to each source Xn. By then knowing the respective distances to each source Xn, and the known positions of each source Xn, at s.4.6 it then becomes possible to calculate the relative position of a particular sensor 462 relative to the positions of the sources Xn. At s. 4.8 this position data is stored for sensor n, and at step 4.10 processing proceeds to the next sensor 462 on the fibre. Once a position has been found for all of the sensors 462 on the fiber 32, the processing loop ends.

At this point in time, therefore, the processor memory contains position data for each sensor point 462 along the entire length of the fibre, relative to the known positions of the acoustic sources 48. By knowing that the sensors are connected together by the fibre, the shape of the fibre can be found by interpolation between the found three dimensional spatial positions of the sensors. Moreover, because there is a known spatial relationship between the fiber and any riser to which it is connected or otherwise related, the shape and position of the riser can also be determined. As such, provided the position sampling rate is sufficiently high then movement and changes of shape of the fibre, and hence the riser, can be tracked over time. Tracking movement and changes in shape of the riser allows for monitoring and other analysis, such as accurate fatigue analysis, amongst other things, to be performed in respect of the riser.

Figure 5:
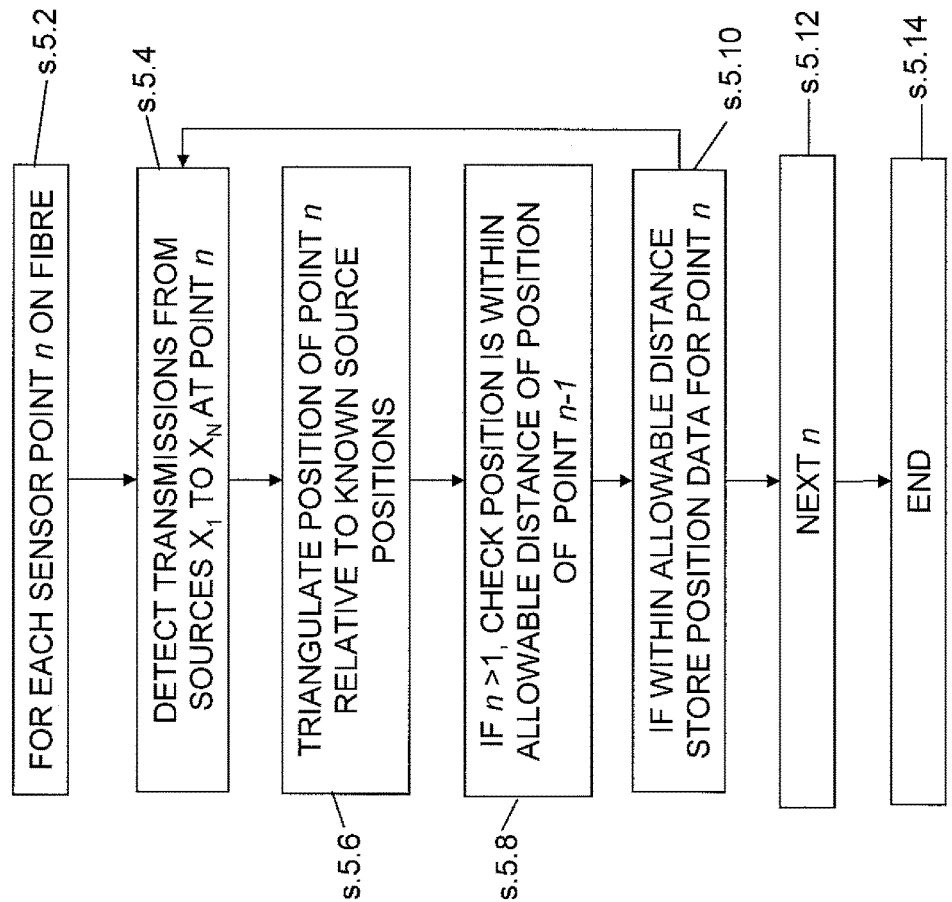
FIG. 5 is a flow diagram of a second embodiment.

A second embodiment that improves upon the first embodiment will also now be described. The second embodiment takes the same operating environment of FIG. 3 as described previously, and operates in a similar manner to the first embodiment, except that within the second embodiment a priori knowledge that the sensor are actually distributed in an array along the fiber is employed as a sense check on a determined position. That is, given that the sensors are 1 m apart along the fibre, the position found for the nth sensor should be no more than 1 m away from the position found for the (n−1)th sensor. Hence, a check can be performed that a determined position is no more than 1 m away from a previously determined position, as the sensors are processed one by one along the fibre. FIG. 5 shows the procedure.

With reference to FIG. 5, when running acoustic positioning program 362 processor 34 acts to determine a position for each sensor 462 on the fibre, as noted, by initiating a FOR processing loop, at s.5.2. Within the loop for a particular sensor at s.5.4 the acoustic transmissions from the acoustic sources Xn (48) are respectively detected, and respective time of flight for each transmission found, to give a set of time data tn. The time of flight for each acoustic signal can then be converted, by knowing the local speed of sound in water, into a distance from each sensor 462 to each source Xn. By then knowing the respective distances to each source Xn, and the known positions of each source Xn, at s.5.6 it then becomes possible to calculate the relative position of a particular sensor 462 relative to the positions of the sources Xn. At s.5.8 a check is then performed, provided the present sensor is not the first sensor on the fibre, as to whether the determined position is within an allowable distance of the previously determined position for the previous sensor in the fiber array. For example, that the presently determined position is no more than 1m from the previously determined position. If this check is met, then at s. 5.10 the position data is stored. If it is not met, then processing returns to step 5.4, and another position is calculated for present sensor n. The processing loop proceeds in this manner until a position has been found for all the sensor points 462, and then the processing ends.

As with the first embodiment, at this point in time, therefore, the processor memory contains position data for each sensor point 462 along the entire length of the fibre, relative to the known positions of the acoustic sources 48, and hence the shape of the fibre, and of any structure to which it is attached, can be determined.

Thus far, the second embodiment has made use of the fact that the sensors are connected in a line array in a limited way only, to perform a sense check on a determined position. In the first embodiment, no use was made of this a priori information. In the preferred third embodiment, however, much greater use is made of the fact that the sensors are connected in a line array, in order to be able to find direction to a particular acoustic source 48, rather than simply distance. By finding direction to a source, fewer sources are required to find a position, specifically as many sources as there are degrees of freedom of movement of the sensor.

FIGS. 6 and 7 illustrate the concept of the third embodiment. Specifically, contiguous groups of sensors 462 along the fiber 32 are grouped together into a virtual small line array sensor 62. An incident acoustic wave incident on the line array sensor 62 will cause an output from each of the sensors at different times, dependent on the angle of incidence of the wave. Hence, as shown in FIG. 6, an incident wave 64 incident on line array 62 at the angle shown will first cause a signal from sensor 622, followed by sensor 624, 628, and finally 630. Moreover, the time delay δ between each sensor being triggered is a cosine function of the direction of travel of the wave, whereby the angle of incidence of the wave can be determined from the order in which the sensors give an output and the time delay between sensor outputs along the array. In this respect, it is assumed that the array size is small enough so as to be considered to be in the far field of the incident wave.

Figure 9:
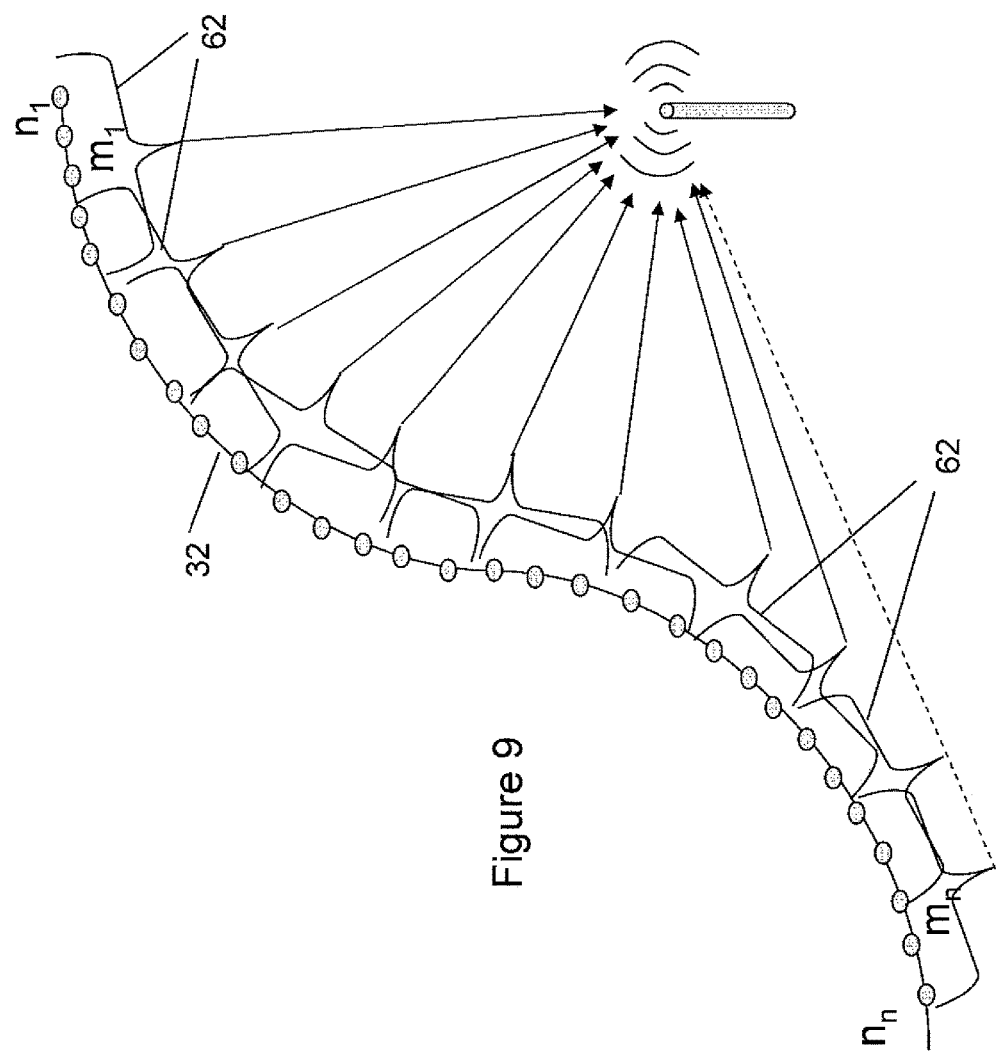

FIGS. 8 and 9 illustrate the application of the above in the third embodiment. In FIG. 8, a plurality of contiguous virtual small line array sensors $m_n$ 62 are formed along the fiber 32. When a signal from an acoustic source 48 is incident thereon, each array is able to determine a direction to the source using the phase delay of the incident wave across the small array, as described above. In Figure the arrays are contiguous, such that if there are, say, 5 sensors in each array, then there are n/5 virtual small line arrays formed. However, because a single direction is found for each array, it might be the case that this does not give a high enough spatial resolution for the shape monitoring (it would give a position for every 5 m array, rather than every 1 m). Therefore, if more position points are found, additional virtual small line arrays may be found by overlapping the arrays, as shown in FIG. 9. Thus for example, each sensor point 462 may be a member of more than one, and up to several, virtual small line arrays 62. A direction to a source can be found for each small line array.

Moreover, the small line arrays are virtual because they are formed simply by processing the signals from the sensors 462 that are members of an array together. Hence, the virtual arrays may overlap significantly by having many of the same sensors as members.

Figure 11:
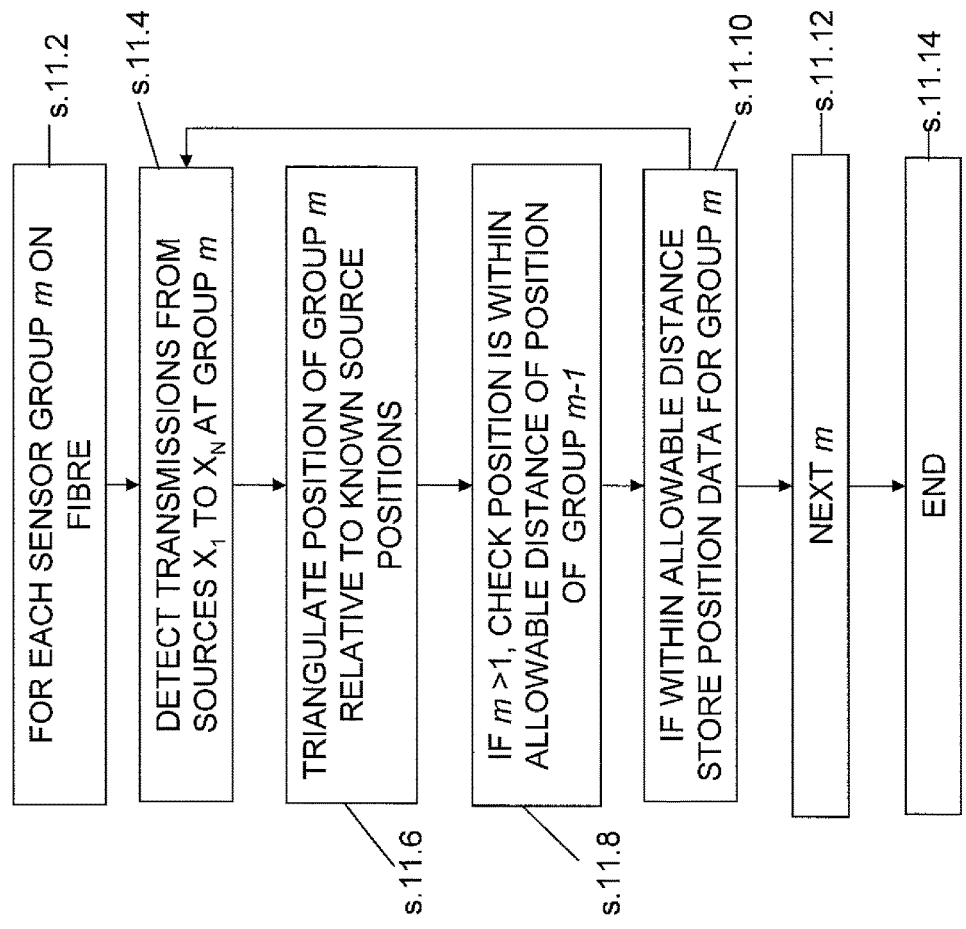
FIGS. 10 and 11 are respective flow diagrams illustrating the operation of the different variants of the third embodiment.
Figure 10:
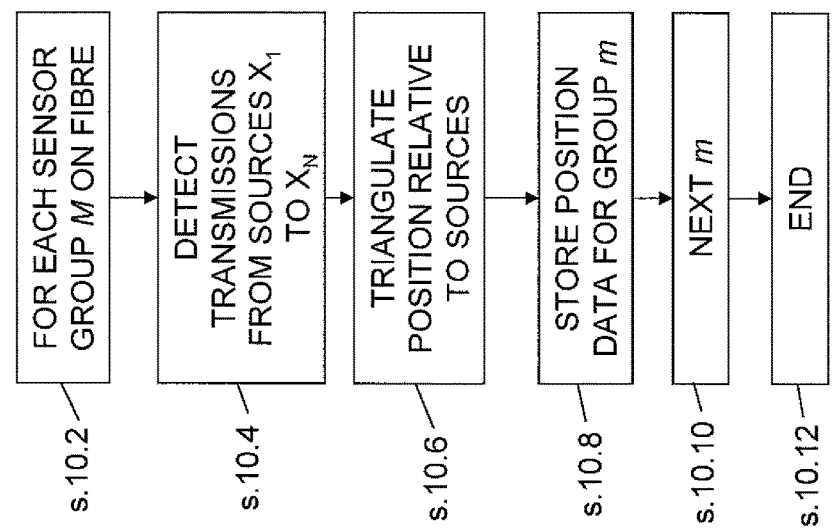

FIGS. 10 and 11 illustrate two ways in which the virtual small line arrays may be used to find position data for the whole fibre. In the embodiment of FIG. 10, when running acoustic positioning program 362 processor 34 acts to determine a position for each line array m on the fibre, as noted, by initiating a FOR processing loop, at s.10.2. Within the loop for a particular line array at s.4.4 the acoustic transmissions from the acoustic sources Xn (48) are respectively detected, and respective directions to the sensors found. The position of each line array can then be found, by taking the position solution which fits to all the found direction solutions. At s. 4.8 this position data is stored for line array m (62), and at step 4.10 processing proceeds to the next array m on the fibre. Once a position has been found for all of the line arrays on the fiber 32, the processing loop ends. Note that the line arrays may be contiguous, as shown in FIG. 8, or overlap, as shown in FIG. 9.

At this point in time, therefore, the processor memory contains position data for each line array 62 along the entire length of the fibre, relative to the known positions of the acoustic sources 48. By knowing that the line arrays form part of the fibre, the shape of the fibre, and hence any riser to which it is connected or otherwise related, can be determined, by examination of the found three dimensional spatial positions of the line arrays. As such, provided the position sampling rate is sufficiently high then movement and shape of the fibre, and hence the riser, can be tracked over time.

FIG. 11 illustrates a further embodiment being a modification of the embodiment of FIG. 10. Here, s.11.2 to 11.6 are the same as steps. 10.2 to 10.6 described above, but at s. 11.8 a position sense check is performed to determine whether the calculated position for an array is allowable given the already determined position of the previous array. For example, it will; be known in advance what will be the maximum distance between the same points, e.g. the centre of each array. For contiguous arrays this may be, for example, 5 m, whereas for overlapping arrays it may be less, say 1 m or 2 m. Hence, if it is determined that the determined position of array m is too far from the positions determined for array (m−1), then the position for array m is calculated again. In this way, a sense check is performed as the array positions are found along the fibre.

Once a position has been found for each array then at that point in time it becomes possible to determine the shape of the fibre, and hence any structure to which it is attached. Moreover, by taking position samples at a high enough rate then movement of the fiber (and hence the structure) can be monitored.

Further operational considerations for the acoustic positioning system of the above described embodiments will now be described.

The operating limitations for sonar systems can be understood using the Sonar Equation $$SL-TL>NL-DI+DT \qquad 1.$$

where SL is the Sound Level of the source, TL is the transmission loss through the medium, NL is the noise level, DI is the Directivity Index, and DT is the Detection Threshold. All units here are in decibels relative to the standard reference intensity of a 1 μPa plane wave. Each of these quantities is now considered individually. This analysis uses the method well-known to practitioners of underwater acoustics as described in by Urick (Urick R. J., 1967).

Sound level

The projector to be used for this system should be an off-the-shelf transducer. Anticipating that the system will work best at low frequencies and high power (as per the analysis to follow), Silixa suggests 180 dB re 1 μPa as a working number for the sake of this study. This level would be high, but not unreasonable, for a low frequency, long baseline (LBL) system of the type used in deep water positioning.

Transmission loss

Transmission loss in the water comes from two principal sources: propagation spreading and material loss. Spreading is the term used to describe the effect of the reduction in signal level which occurs for non-planar sound as the signal diverges along its propagation path. Since the same sound energy must cover successively larger 'shells' over time, the signal intensity over a given area reduces with distance from the source. This can be characterized as described in the table below.

TABLE 1

Transmission loss as a result of geometric spreading

| Spreading type | Intensity varies with radius r as | Transmission loss (dB) |
| --- | --- | --- |
| None | $r^0$ | 0 |
| Cylindrical | $r^{-1}$ | 10 log r |
| Spherical | $r^{-2}$ | 20 log r |

For propagation in the ocean, it is appropriate to assume spherical spreading. Therefore, the transmission loss caused by spreading has been assumed to be 20 log r for the sonar equation calculations shown later in this document.

Along the propagation, transmission loss as a result of material losses path increases with frequency. This can be approximated using the method of (Thorp, 1966).

$$\alpha = \frac{0.1 f^2}{1+f^2} + \frac{40 f^2}{4100+f^2} + 2.75 \times 10^{-4} f^2 + 0.003. \qquad 2$$

where f is frequency and α is absorption in units of dB per kiloyard. This equation indicates why most LBL systems work at low- and mid-frequency. The increased absorption at higher frequencies results in lower SNR when operating in that regime.

Noise level

There are two principal sources of noise in the proposed system: self-noise from the DAS system, and oceanic ambient noise. In the below the noise from the DAS is assumed to be roughly as loud as the noisy ambient sea.

Figure 20:
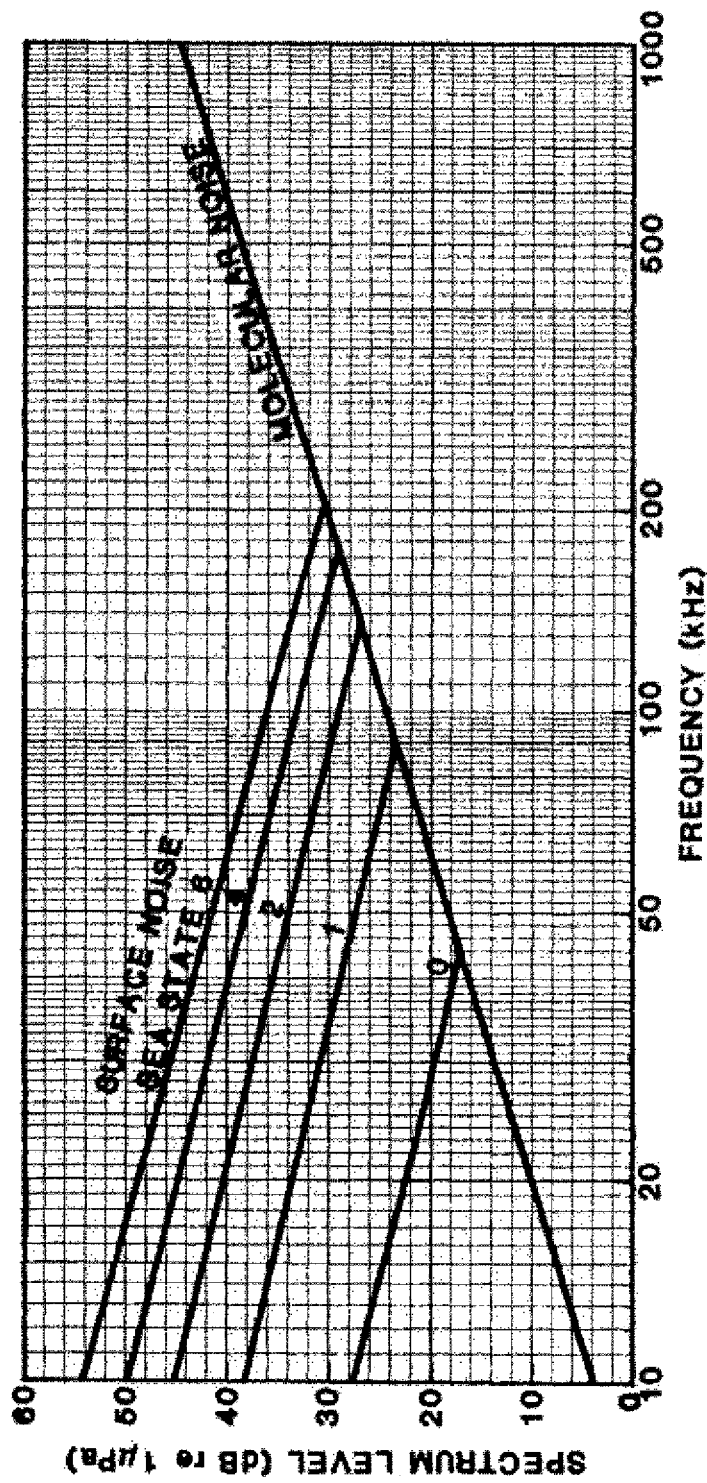
FIG. 20 is a graph showing ambient noise spectra for the deep ocean. Low frequencies according to Knudsen, and molecular noise curve according to Mellen. Reproduced from (Urick R. J., 1984).

The subject of ambient noise level in the sea has been a topic of interest to researchers in both shallow and deep water for several decades. The classic starting point for modern discussions on ambient noise in deep water are the well-known Knudsen curves (Knudsen, Alford, & Emling, 1948), which show how the ambient noise spectrum varies with sea state. The work of Knudsen indicates a descent in noise at a rate of about 20 dB/decade above about 100 Hz. While this trend is well suited for low frequency noise estimation (though it should be noted that Knudsen neglected the effect of rain-induced bubble entrainment in the range of 14 kHz), but for frequencies above about 50 kHz, thermal noise is usually considered to be a significant source of disturbance (Mellen, 1952). The degree to which the thermal noise work of Mellen is relevant to the present invention is still unclear, but it is nonetheless included in the spectrum shown in FIG. 20 to counter the apparent conclusion from Knudsen that noise always decreases with increasing frequency.

For the calculations performed here, Beaufort State 5 (winds 18-24 mph with many whitecaps visible) has been assumed.

Directivity index

Figure 21:
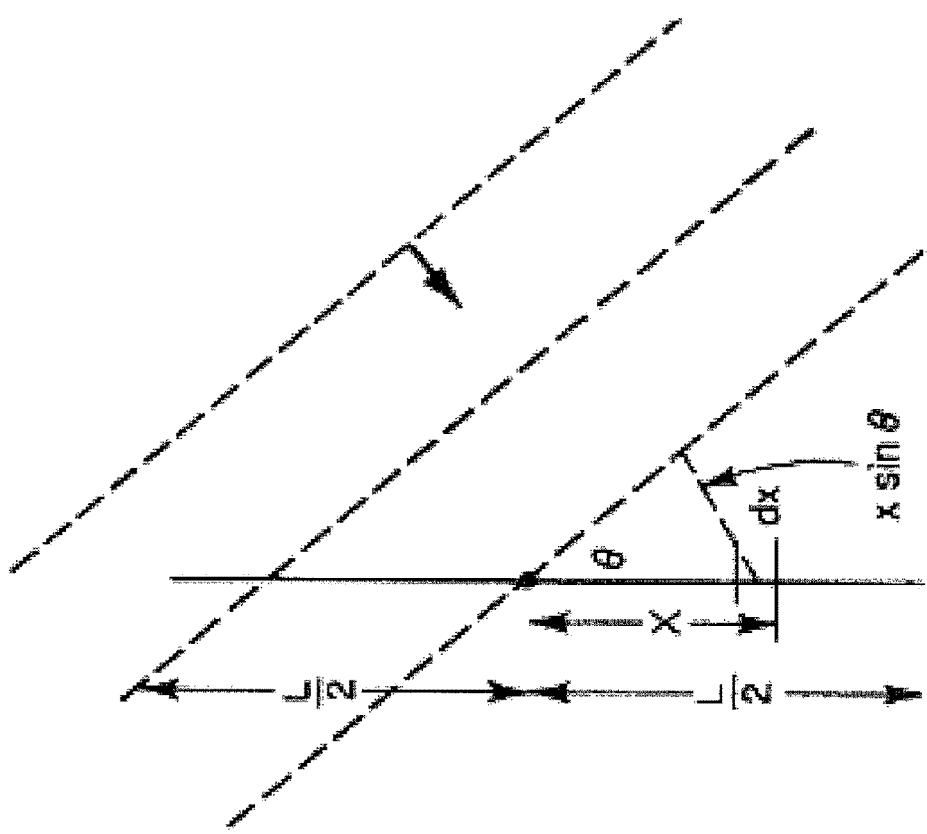
FIG. 21 is a diagram showing the geometry of a line array after Urick (Urick R., 1983).

Directivity index is usually treated as an advantage in the sonar equation, as it can be used to reduce the volume over which the acoustic signal spreads. However, if the receiver in a system of the type used for this application (known as a passive monostatic system) is oriented such that the transducer is oriented away from the direction of propagation, then the directivity can be a disadvantage. For retrofit installations where the cable is orientated along the riser and at long ranges from the transponders, where the cable is essentially parallel to the path of propagation, that is indeed the case. The receiver, the optic fiber DAS, is in effect what is known as a continuous line array. The directivity for a continuous line array is well-known, and shown in FIG. 21.

Urick calculates the voltage output V for a line array of length L (illustrated above) by considering the contribution of a differential element as $$dV = \frac{R}{L} e^{(\frac{j2\pi}{\theta})x \sin\theta} dx. \qquad 3$$

where the quantities are as illustrated in 21. The total voltage can then be calculated by integrating over the length of the array.

$$V = \frac{R}{L} \int_{-\frac{L}{2}}^{\frac{L}{2}} e^{(\frac{j2\pi}{\theta})x \sin\theta} dx. \qquad 4$$

The beam pattern b(θ) will be the square of V normalised so that the maximum of b(θ)=1, which gives the well-known result $$b(\theta) = \left(\frac{V}{R}\right)^2 = \left[\frac{\sin\left[\left(\frac{\pi L}{\theta}\right)\sin\theta\right]}{\left(\frac{\pi L}{\theta}\right)\sin\theta}\right]^2. \qquad 5$$

Since the system will be receiving signal along the length of the riser, and hence away from the main lobe, it is informative to apply the minimal averaging length in order to overcome the signal suppression which will result. Currently, the minimum Silixa iDAS resolution is 50 cm. Further, the undesired suppression can be minimized by increasing the wavelength of interest. To illustrate the combined result of these two factors, the directivities for 1 m and 50 cm systems operating at 10 kHz and 50 kHz have been shown in FIG. 22.

Figure 22:
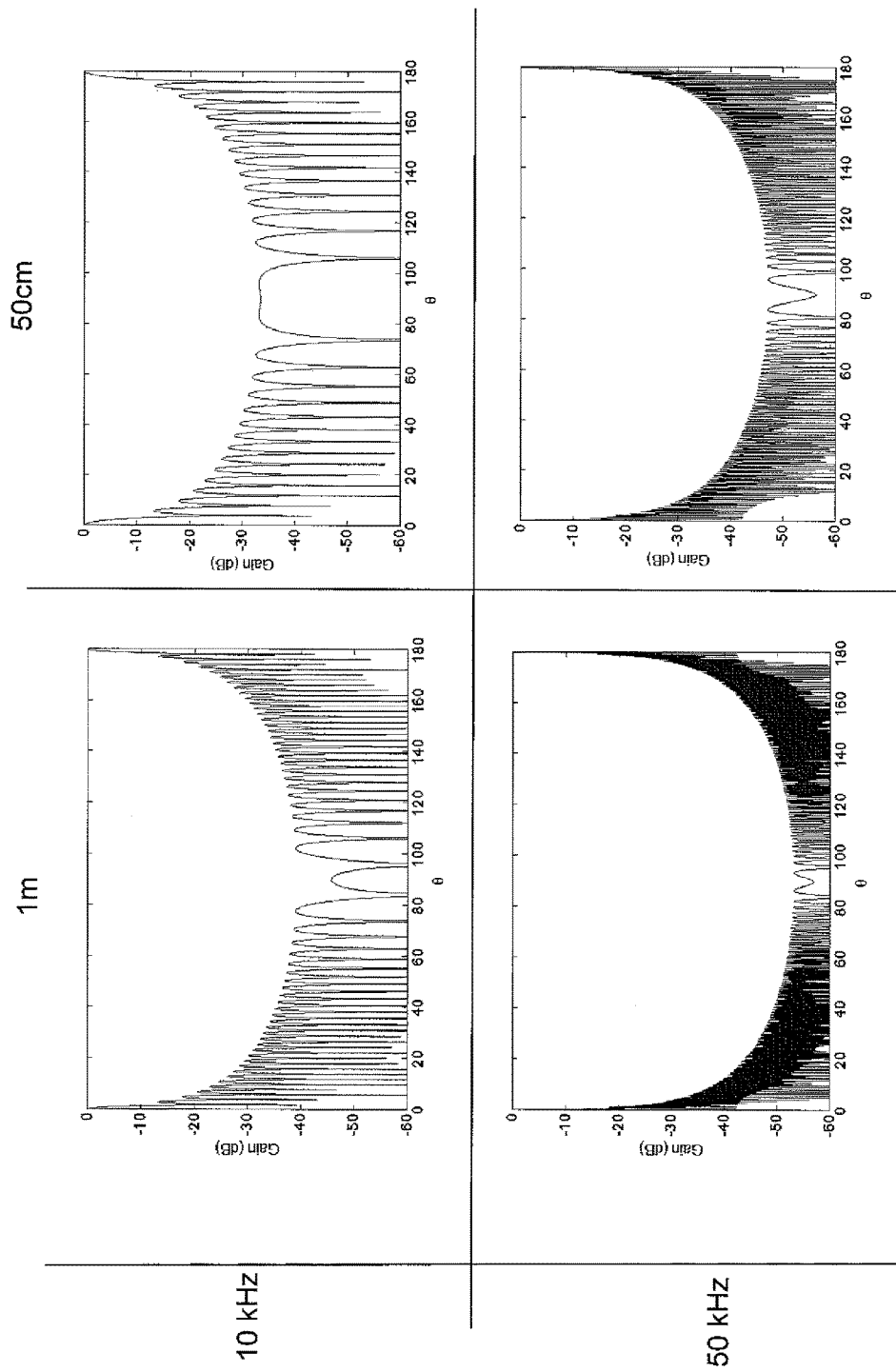
FIG. 22 is a series of graphs showing the effects of spatial resolution and operating frequency on the directional gain of a DAS when employed in a straight-line configuration

FIG. 22 can be studied in the context of this discussion by considering the worst-case scenario shown in each figure, as the highest suppression for a receiver of this type occurs at endfire (that is, where the signal ray is oriented along the length of the receiver). For theH 1 m resolution, the 10 kHz and 50 kHz cases respectively give −46 dB and −55 dB suppression at endfire)(90°), while for the 50 cm resolution, 10 kHz and 50 kHz result in −32 dB and −54 dB respectively. These findings illustrate the outcome expected when considering the derivation above: for the application at hand, it is optimal to use as fine a DAS spatial resolution as can be delivered, and a driving signal with as low of a center frequency as is possible. Note that a reduction in driving frequency will result in a corresponding increase in background noise level as per the previous discussion on ambient noise, but that the resultant benefits in directivity drive the optimal driving frequency to the region of about 1 kHz. For the purpose of the calculation performed below, a 50 cm resolution and 10 kHz operating frequency are assumed, giving a directional suppression of −32 dB.

It should be noted that creative fiber installations, such as those taking advantage of spiral cable geometries, could be used to overcome some of the challenges introduced as a result of geometric signal averaging.

Detection Threshold

Dynamic positioning of a cable via an optic fiber DAS as described in the above embodiments can be performed using the same signal processing techniques that are used with standard hydrophones as discussed above. This section is used to perform an analysis which helps to identify the practical factors which are most critical in determining a practical Signal-to-Noise (SNR) ratio via an analysis of the system. This SNR can then be set as a Detection Threshold in the sonar equation. Since the system is taking advantage of the power offered by having a large set of sensors, and not just a single sensor, it is advantageous to use an array processing method. Further, the problem is well constrained, as the upper and lower termination limit of the riser are possibly at a known location. An additional refinement can be made because the rough shape of the riser can be estimated. The analysis here begins with the solution of Fistas and Manikas (Fistas & Manikas, 1994) (applicable to the case where no assumptions are made concerning the riser shape), and then incorporates geometric assumptions by employing the method of Kamil (Kamil, 2011). Finally, the method of Kamil is used to estimate the maximum horizontal system resolution. In this discussion, two types of resolution are relevant: vertical resolution, and horizontal resolution. Vertical system resolution refers to the effective sensor spacing enforced by the DAS. Horizontal system resolution is the positioning precision that results from the calibration algorithm. It should be noted that the analysis here is based on the use of three simultaneously present sources, at least two of which operate at different azimuth angles.

If a source is transmitting from a known location to an array, the signal received by an array of N sensors can be modeled as:

$$\underline{x} = \sqrt{P_s}\underline{S} + \underline{n} \qquad 6.$$

where $\underline{S}$ is the manifold vector or source positioning vector (SPV). The SPV is a mapping of the source locations to different phase delays and gains in the signals received by the array. $P_s$ is the power of the transmitted signal at the array's reference point and $\underline{n}$ is the noise vector.

Far field

Consider a source transmitting a narrowband signal from a known location where the range $\rho_o$ from the array reference point satisfies the following relation:

$$\rho_0 \gg \frac{2D^2}{\lambda}. \qquad 7$$

where D is the largest dimension of the array or the array aperture and $\lambda$, is the wavelength. This source is considered to be in the far-field of the array. Thus, the amplitude of the received signal is approximately constant across the array (this is particularly a valid assumption if we consider short section of the riser (as can be seen from the far field condition)). In the far-field case, the SPV used in Equation (6) can be modeled as:

$$\underline{S} = \exp(-j\underline{r}^T\underline{k}) \qquad 8.$$

where $\underline{r}$ is an 3×N matrix containing the locations of the sensors (in 3D) in the array. From Equation (7), it can be seen that the magnitude of the manifold vector is $\sqrt{N}$.

If the sensor locations are imperfectly known, $\underline{S}$ can be used to denote the nominal SPV (with assumed locations). Using Equation (7), the true SPV $\hat{\underline{S}}$ which takes into account the errors in the nominal values can be modeled as:

$$\hat{\underline{S}} = \exp(-j\underline{\tilde{r}}^T\underline{k}) \odot \underline{S}\text{diag}(\exp(-j\underline{\tilde{r}}^T\underline{k}))\underline{S} \qquad 9.$$

$\underline{\tilde{r}}$ is a matrix that contains the uncertainties in the array sensor locations, whereas $\text{diag}(\underline{V})$ denotes a diagonal matrix with $\underline{V}$ in its diagonal elements. The superscript $(\square)^T$ denotes transpose of the vector or the matrix.

From Equations (6) and (7), it can be seen that the amplitude of the signal does not have any information regarding the locations of the sensors. Therefore, the phase delay information is used to calibrate the array and the power of the signal $P_s$ can be assumed without loss of generality to be equal to unity. The covariance matrix of the received signal can be modeled as:

$$\underline{R}_{xx} = \hat{\underline{S}}\hat{\underline{S}}^H + \sigma^2\underline{I} \qquad 10.$$

where $\sigma^2$ is the noise power and $\underline{I}$ is the identity matrix. Also, the superscript $(\square)^H$ denotes conjugate transpose of the vector or the matrix.

The knowledge of the source location translates into knowledge of the nominal SPV (based on the assumed sensors locations) i.e. the nominal phase delay information. This is useful in estimating the actual sensor locations. In particular, the covariance matrix is pre- and post-processed by the diagonal matrix $\underline{\Lambda}$ defined as $$\underline{\Lambda} = \text{diag}(\underline{S}) \qquad 11.$$

and is obtained from knowledge of the source location. Using Equation (10), this operation can be simplified to $$\underline{\Lambda}^H \underline{R}_{xx} \underline{\Lambda} \qquad 12.$$

It is common to regard one element as a reference and to assume that its position is accurately known. For simplicity, the first element of the array is taken as the reference element (Note that if this assumption is not satisfied, the estimated array locations will have a translational error dependent on the position of the $1^{st}$ sensor node). Therefore, the vector $\exp(-j\underline{\tilde{r}}^T\underline{k})$ can be modeled as $$\exp(-j\underline{\tilde{r}}^T\underline{k}) = \begin{bmatrix} 1 \\ \underline{u} \end{bmatrix}. \qquad 13$$

where $\underline{u} = \exp(-j\underline{\tilde{r}}^T\underline{k})|_{2:N}$ corresponds to the N−1 elements of the vector $\exp(-j\underline{\tilde{r}}^T\underline{k})$ starting from the second element. Thus, equation (12) can be written as $$\underline{\Lambda}^H \underline{R}_{xx} \underline{\Lambda} = \begin{bmatrix} 1+\sigma^2 & \underline{u}^H \\ \underline{u} & \underline{u}\underline{u}^H + \sigma^2 \end{bmatrix}. \qquad 14$$

It can be seen from the above that one source can be used to estimate the perturbations in the SPV (i.e. $\exp(-j(\_(\_r))^{-T}T\_k))$. However, we are more interested in the perturbations in the actual locations i.e. $\tilde{r}$.

From the knowledge of $\exp(-j\tilde{r}^T k)$, the perturbations can be estimated directly as the following:

$$\exp(-j\tilde{r}^T k) = \exp([\tilde{x}\ \tilde{y}\ \tilde{z}]k) = \underline{b} \qquad 15.$$

The previous equation comprises a set of N−1 equations to solve d(N−1) unknowns where d is the dimension of the coordinate system in which we are interested (3 in the previous equations). The problem is strictly well posed and comprises a system of over-determined equations if $$M \geq d \qquad 16.$$

For example, if for a given array geometry uncertainties can only occur in one dimension, one source is sufficient to estimate the uncertainties. However, for systems with two degrees of freedom (for instance lateral motion and depth), a minimum of two sources are needed to be able to perform positioning accurately. Further increasing the number of sources beyond the problem dimensions d will improve the accuracy of the estimates.

Near Field

The previous analysis can be used to estimate the sensor positions assuming that the far field model is valid. To enforce this condition for the purpose of riser monitoring, the array of sensors has to be divided into smaller sub-lengths along which the far field model can be applied. In (Kamil, 2011), this analysis is extended to near field sources. The principle of operation is similar however, by using the near field model; the amplitude information of the source can be used in addition to the phase information to estimate the source location. Combining these two methods can in general result in much more accurate results and faster convergence rates.

Figure 23:
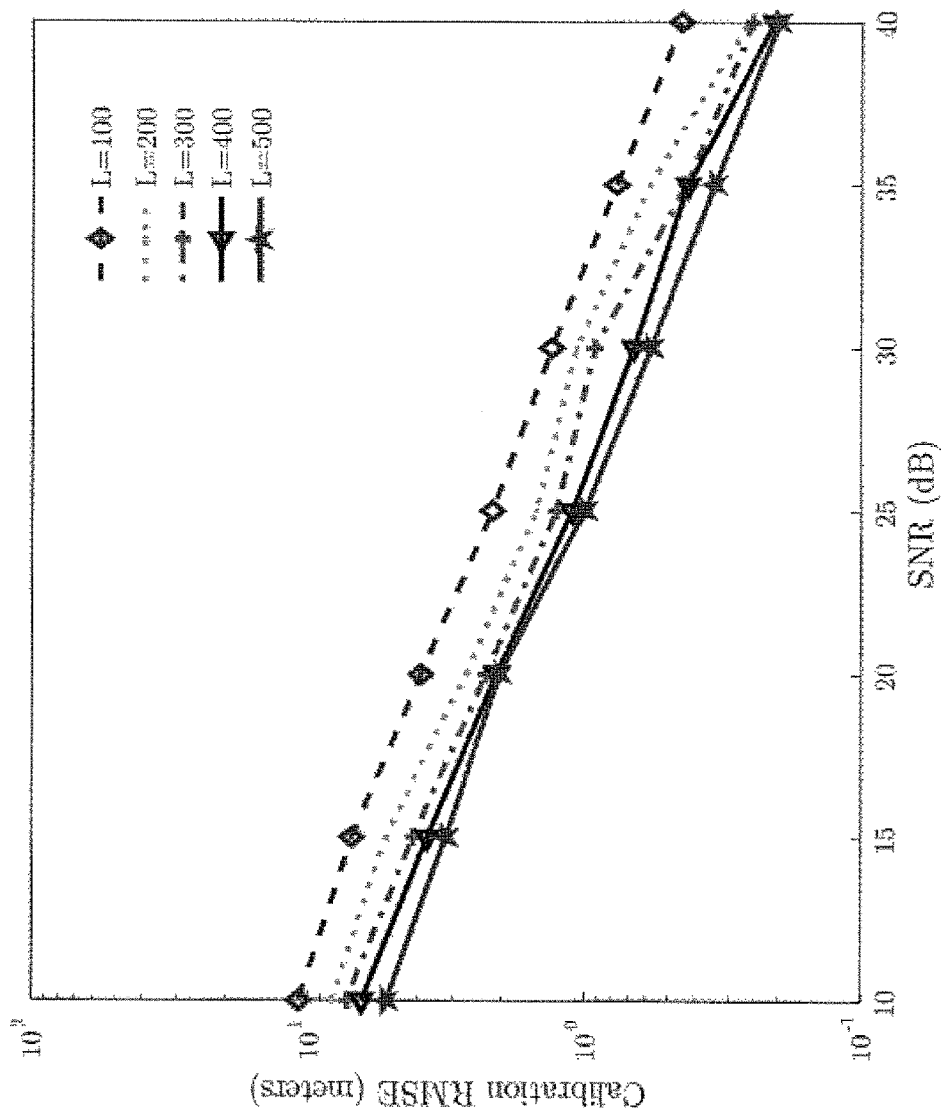
FIG. 23 is a graph that shows that increasing the signal-to-noise ratio and number of snapshots allows high precision to be achieved in the positioning algorithm.

The result of a simulation showing the effect of signal-to-noise ratio, and the number of snapshots used to calculate position is shown in FIG. 23. In this figure, only two sources are used to calibrate an array of 7 sensors. The presented root mean square error is the sum of the RMSE errors in all the 7 sensors. Note that this calibration method has not used any noise reduction technique (e.g. spectral subtraction, Wiener filtering etc.) which can be expected to result in an additional SNR gain of 10-20 dB. The numbers in the legend of the Figure indicate the number of snapshots (samples) used in the calibration calculation. A 10 kHz transponder using signals of length 20 cycles (20 ms) sampled at 20 kHz gives 400 samples per ping, meaning that at least 400 snapshots are achievable per transponder ping shows that similar levels of precision can be achieved for fewer pings, but this is again a function of the signal to noise ratio.

The output from both simulations indicates that a key factor in the determination of the system precision has to do with signal-to-noise ratio. The way in which this factor can be controlled is a topic of discussion next.

As stated above, precision on the order of centimeters is achievable in the acoustic positioning paradigm. It was also seen that the realizable precision is a function of the signal to noise ratio. The signal to noise ratio is actually controlled by the frequency sensitivity, which is in turn a function of both structural considerations as well as directivity for reasons given below.

Even given an acoustically sensitive cable, an unsympathetic cable housing or mounting method will render an optical fiber DAS unable to observe acoustic signals with a SNR sufficient for accurate positioning. This is particularly important when considering the fact that it may be desirable to implement the shape monitoring method of embodiments of the invention on already-existing cables housed within heavily armored umbilical lines. In this configuration, the degree to which the system will be able to observe the signal of interest is currently unknown. It should be born in mind that the structural sensitivity is a function of frequency, and so simply because a given umbilical is insensitive to a particular positioning transducer, it cannot be assumed that it is insensitive to all transducers. Nonetheless, for present purposes it is advisable to use a cable of both excellent acoustic sensitivity and high wear in challenging environments. Further, such a cable should be installed in a way so as to avoid the undesirable effects of directional signal suppression.

Sonar Equation Model

By considering each of the parameters discussed in the context of the sonar equation, and generating a model on their basis, it can be established whether it is possible to use the optic fiber DAS acoustic positioning capability in the field, and to what range. The result of this exercise is shown below in Table 2. (assuming 50 cm spatial resolution, and a modest source directivity of 3 dB). In the first row, the SNR has been reduced to 10 dB (assuming knowledge of the transducer ping signal, this could be achieved via a Wiener filter). In the second row, the SNR has been reduced to the level required in the case where the system is effectively 'blind' e.g. No knowledge concerning the transducer signal is available. In the right hand column is calculated the maximum range for the case where an operating frequency of 50 kHz is used with an SNR of 10 dB.

| f (kHz) | SL | TL Spreading | TL Absorption | TL Cable | TL Combined | NL Combined | DI | DT | Maximum range (m) |
|---|---|---|---|---|---|---|---|---|---|
| 10 | 180 | 79 | 9 | 6 | 94 | 46 | −29 | 10 | 9000 |
| 10 | 180 | 66 | 2 | 6 | 74 | 46 | −29 | 30 | 2000 |
| 50 | 180 | 64 | 22 | 6 | 91 | 46 | −29 | 10 | 100 |

It has been shown that high levels of precision in acoustic positioning can be achieved, particularly when taking advantage of the fact that a DAS senses not just a single point in space, but an entire array of subsequently adjacent receivers. The simulation here has been performed in the case where the system is being run from startup. In the case where data is being continuously updated, the same analysis It is clear from the above that the greatest deficit to system performance in this scenario is the directivity index resulting from the fiber configuration. Custom cables can be provided which can overcome this challenge.

Distributed Temperature Sensing

Important to the acoustic propagation model used in the positioning embodiments described above is an estimate of the sound speed profile within the water column. This can also be sensed via an optical fiber based system, such as that commercially available from Silixa Limited, Elstree, United Kingdom, and known as the Ultima distributed temperature sensor (DTS). The DTS system supplied by Silixa can function in parallel with the optic fiber DAS along a multimode fiber within the same cable, and gives the temperature with a resolution of 0.01° C. every 25 cm. The temperature sensor is an important component of the subsea distributed acoustic positioning system of the above embodiments, to give a water column temperature profile from which the speed of sound in the water can be deduced. It should be noted that, in a purpose designed cable, it is straightforward to introduce both multimode mode and singlemode cable. This will enable spatially coincident temperature and acoustics measurements respectively via a single efficient package.

Dynamic Vibration Modelling

A further embodiment of the invention will now be described in more detail, relating to using the optic fiber DAS for detecting vibrations in the structure to which the fiber is attached. This embodiment was mentioned previously in the overview section above.

As discussed previously, an optic fiber DAS, such as the Silixa iDAS, is a vibroacoustic sensor which can report the dynamic field at intervals of one meter along the entire length of a fiber optic cable up to several kilometers in length. In the previous embodiments it was shown how such a sensor could be used as the sensing mechanism for a distributed acoustic positioning system based on acoustic signal output at tens of kilohertz. In the present embodiment we describe how the same fiber being used for acoustic positioning sensing can simultaneously be used for dynamic vibration monitoring.

Consider a fiber optic cable suspended between two clamps and imparted with a mechanical impulse. The mechanical impulse will introduce a strain which can be observed using a differential strain measurement method. The dynamic range of a DAS, such as the Silixa iDAS, allows it to measure differential strain, and it can therefore observe the time history of this strain disturbance. If for instance this dynamic strain has a center frequency on the order of Hz, and this same cable is imparted with sound of a higher frequency (say, on the order of kHz), then a simple series of band pass filters can be used to distinguish the vibration-induced strain from the acoustic excitation. In this way, it is possible to facilitate both vibration monitoring and acoustic positioning along a single fiber. Hence the optic fiber DAS can be used to detect low frequency resonant type vibrations in structures such as risers, buildings, antenna towers, or any other large structure which may have resonant vibration modes. Other, non resonant, mechanical vibrations may also be detected.

Figure 13:
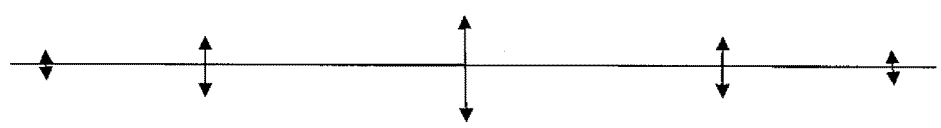
FIGS. 12 and 13 illustrate example resonant modes in a structure tethered at both ends.
Figure 12:
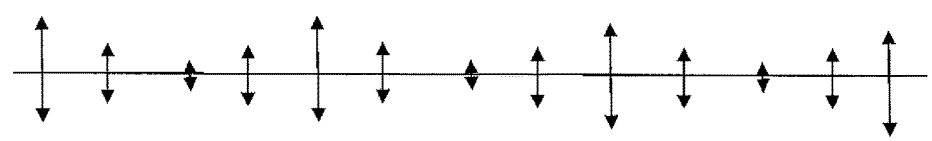

FIGS. 12 and 13 give examples of possible resonant modes of a structure such as a riser. FIG. 12 shows a higher order mode, and FIG. 13 shows a fundamental resonant mode. In the case of a riser the structure is tethered at the top and bottom, and hence resonates substantially like a guitar string (although of much lower frequency). Structures tethered at one end, such as a tall building or tower may simply resonate by swaying from side to side. In addition, any structure may also be subject to non-resonant mechanical vibrations, which may also be detected by the present embodiments.

In the previous embodiments relating to acoustic positioning, it was mentioned that the installation of fiber optic cable, and particularly the cross-section of the assembly suspending that cable, will influence the sensitivity of that fiber to the acoustic field. The same principal holds true for vibration monitoring, but the present embodiment relating to vibration sensing is more robust to the specifics of cable design than is the case for acoustic sensing. For instance, as an example embodiment, consider an armored optical cable suspended within a subsea umbilical line, where the umbilical has multiple additional layers of armor. The umbilical cable in this example embodiment is suspended by clamps mounted on the exterior of the riser cross-section, such that the walls of the umbilical are in direct contact with the ocean. The clamps are at intervals of approximately 10 m. High frequency signals passing from the environment to the fiber are likely to be highly attenuated in this scenario. However, the umbilical is actually very well-coupled to the riser from a vibration standpoint. In this context, 'well-coupled' means that the fundamental mechanical resonance of the clamp is many orders of magnitude higher in frequency than the vibrations of interest. As a result, the clamp will tend to behave in the mass-controlled motion regime, which is essentially quasi-static. Further, the low ratio of the cable cross-sectional mass to that of the riser dictates that for wavelengths much longer than the inter-clamp spacing, high sensitivity sensing can be achieved on the cable. In this respect, the physical sampling of systems is similar to the digital sampling of temporal events, in that at least two points per cycle are needed to resolve a wave. For a clamp spacing of 10 m, it is suggested that an optic fiber DAS such as the Silixa iDAS could be able to resolve waves as short as 30 m.

Figure 15:
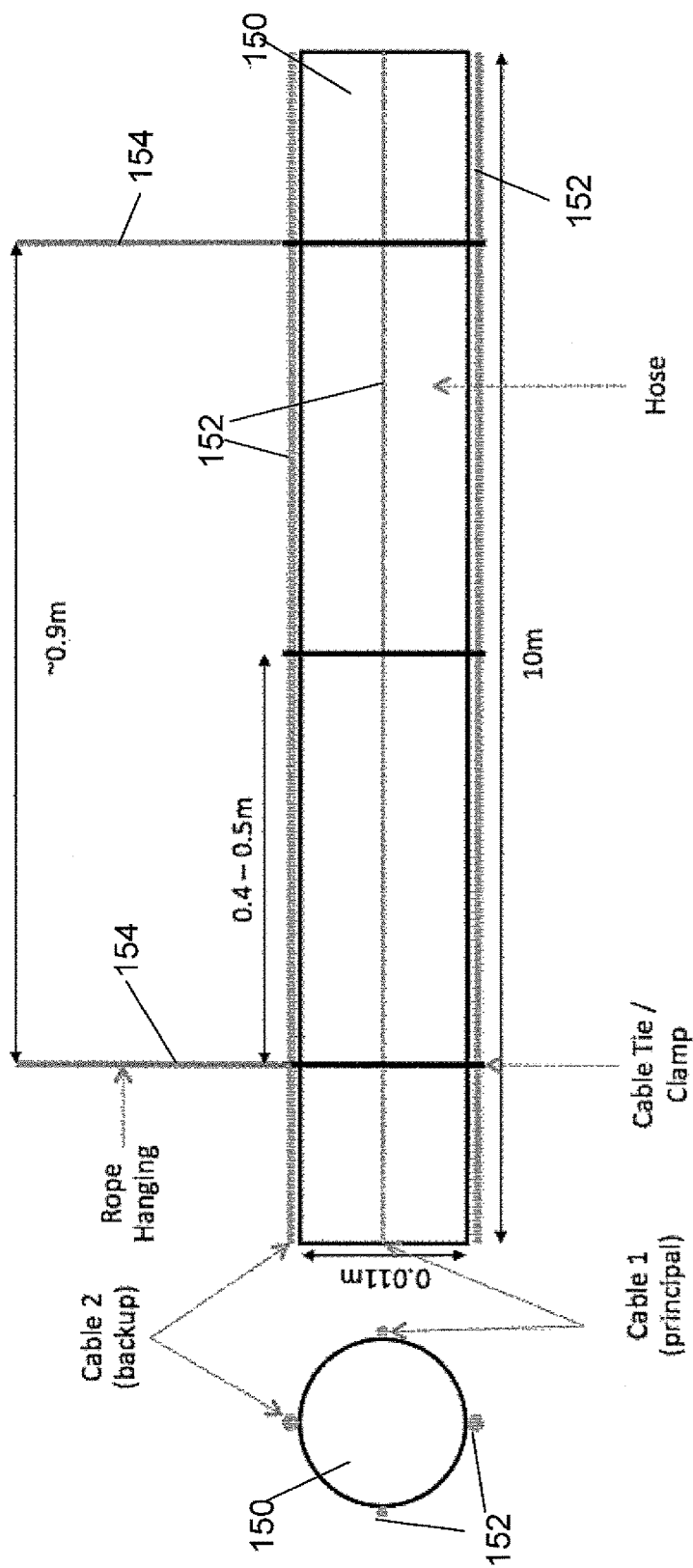
FIG. 15 is a diagram of an experimental rig forming a further embodiment of the invention.

An example test embodiment to test the functionality of such a vibration sensor is shown in FIG. 15. A key motivation for this experiment was establishing the degree to which vibrations below about 1 Hz can be sensed using an unmodified DAS. The rig designed was made to resemble a riser with optical fiber cable mounted along its length. The cable was laid along a hose length 150 in four runs 152 and joined to the flexible hose using cable ties at 1 m intervals. The four separate runs of optical cable 152 were distributed radially as indicated in FIG. 15, with one run each at 0°, 90°, 180° and 270°. The purpose of using multiple cable runs was to demonstrate that the optic fiber DAS is capable of determining the sections in compression and tension simultaneously. The hose was suspended from a height of 4 m using nylon rope 154. The optical cable used for these experiments was hermetically sealed cable of the type appropriate for a deep-sea installation. The energy input for this test was provided by means of an engineer who displaced the cable in the horizontal plane with a zero-to-peak amplitude of approximately 1 diameter at the following frequencies: 0.5 Hz, 0.05 Hz, and 0.0083 Hz (the last frequency corresponding to a period of 2 minutes).

It should be noted that, for the purpose of this feasibility study, no modifications were made to the optic fiber DAS to increase its suitability for low frequency measurements.

Figure 16:
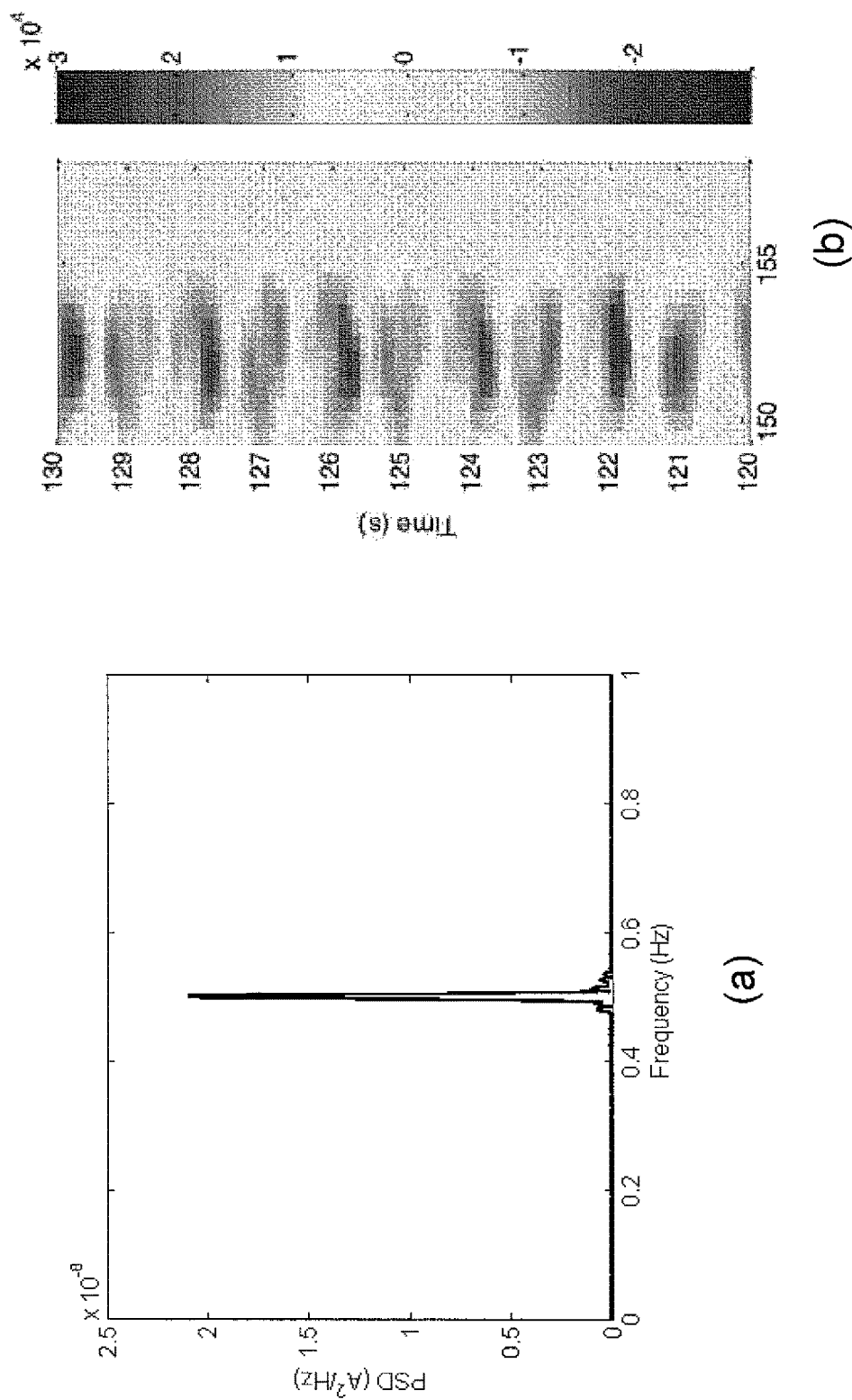

The results of this experiment are shown in FIGS. 16, 17 and 18, which respectively show the results for a driving vibration at 0.5 Hz, 0.05 Hz, and 0.0083 Hz. Several interesting features of the system are revealed by the experiment. At 0.5 Hz (see FIG. 16), the output is clearly evident in both the time and frequency domains. The signal-to-noise ratio of the results in the time domain appears to decrease with frequency. This is a result of two factors: driving method and optical algorithm performance. The driving method used for these experiments was purely manual. That is, to drive the hose, an individual with a stop-watch slowly manipulated the experiment at the mid-section between the clamps. This method is significantly easier to control at 0.5

Hz than at 0.05 Hz and below, as no apparent rhythm is available below about 0.5 Hz. As a result, the input signal at the lowest frequencies is not truly sinusoidal, and some signal distortion exists. Despite the decrease in signal-to-noise ratio with frequency in the time domain, the frequency domain results indicate clear detectability of the 0.05 Hz (see FIGS. 17) and 0.0083 Hz (see FIG. 18) signals. The presence of some harmonics is expected as per the input signal distortions described above. A decrease in signal amplitude is seen with frequency. In addition, at frequencies below about 0.1 Hz, temperature drift occurs over the cable as a function of time. It is likely in the future that signal processing improvements can be made to improve the detection of such low frequencies by an optic fiber DAS.

Figure 14:
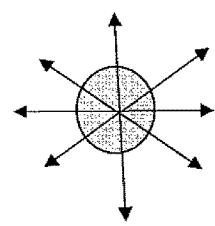
FIG. 14 shows possible oscillation directions of a structure.
Figure 19:
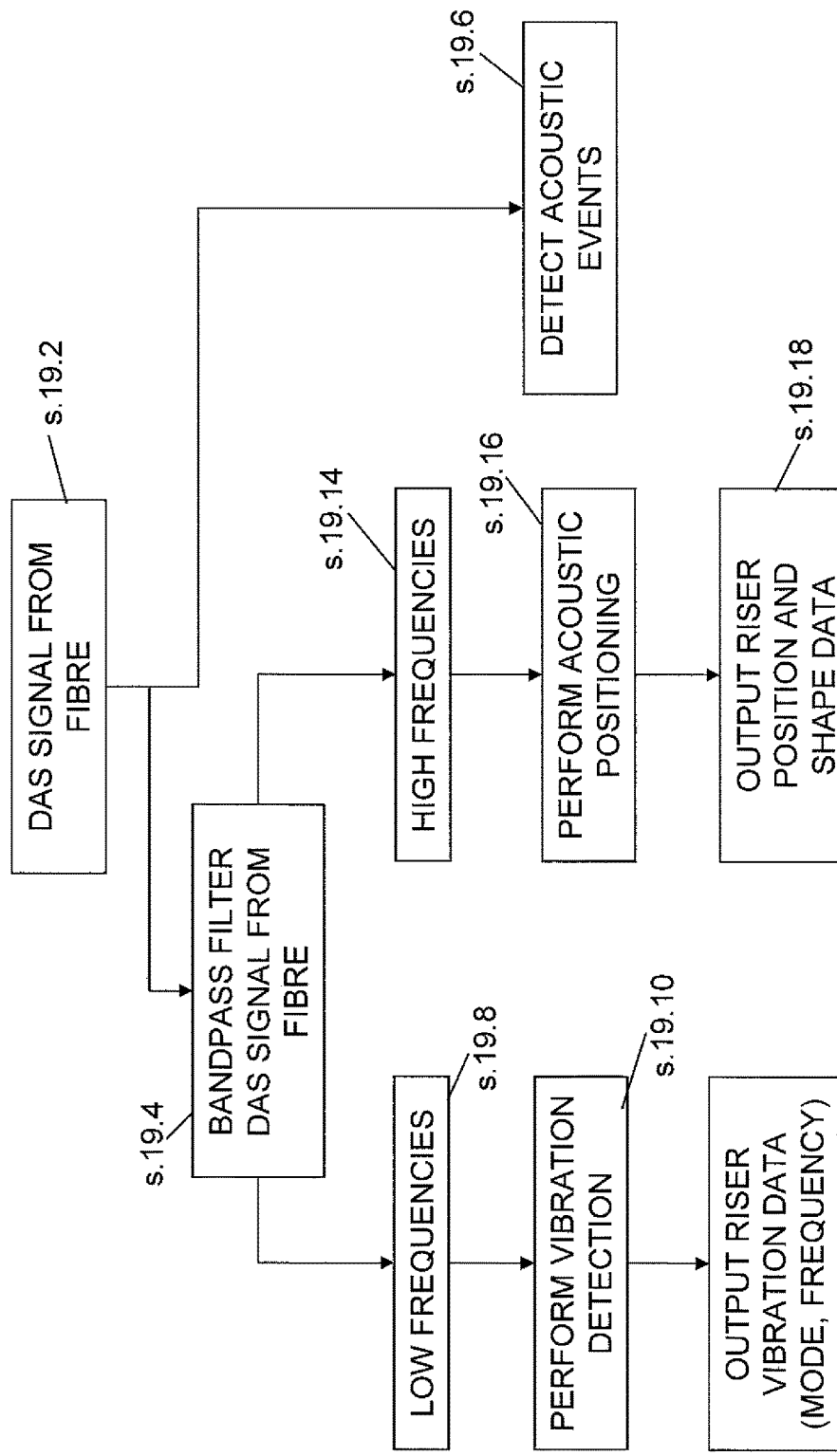
FIG. 19 is a flow diagram illustrating the operation of a further embodiment of the invention.

From the above, however, it becomes apparent that an optic fiber DAS such as the Silixa iDAS that is deployed to perform acoustic sensing can also be used, with no modification, to detect low frequency mechanical vibrations in a structure to which the fiber is attached. This is because the physical effect on the fiber in terms of altering Rayleigh backscatter is obtained whether the fiber is within a vibro acoustic (sound) field, or whether it is subject to actual mechanical vibration (which may or may not be accompanied by acoustic vibration). Thus, in some embodiments of the invention, and as shown in FIG. 19, the DAS signal from the fiber (s.19.2) may be frequency filtered (s.19.4), for example by respective band pass filters or low and high pass filters to split the signal into low frequencies (s.19.8) and high frequencies (s.19.14), the low frequencies typically being of the order of a few Hz and resulting from mechanical vibrations in the structure, and the high frequencies being typically in the kHz range, and resulting from the frequencies used by the acoustic sources 48 in an acoustic positioning system. The low frequencies are then used at s. 19.10 and 19.12 to perform vibration detection in the structure to which the fiber relates, and vibration data such as mode, and frequency can be obtained. The high frequencies are used at s. 19.16 and 19.18 to perform acoustic positioning in accordance with any of the previously described embodiments, to obtain data relating to the position of the structure to which the fiber relates, and its shape. Moreover the two systems can complement each other, in that, whilst the vibration detection system may detect the presence of vibrations and their frequency, it will not necessarily detect the direction of oscillation of the vibration. In this respect, as shown in FIG. 14 a structure tethered at both ends may oscillate in any direction. However, by combining the output data of the vibration detection with the location and shape data from the acoustic positioning system, then knowledge is also obtained as to vibration oscillation direction. Such information should prove useful in fatigue analysis of the structure.

In addition, in some embodiments of the invention, in addition to acoustic positioning and vibration detection, the optical fiber DAS can also provide passive acoustic data relevant to the structural health of the structure to which the fiber relates, as shown at s. 19.6. This capability can be used to identify for instance high amplitude events linked to crack propagation or, where the structure is a riser, riser support disengagement. The technology can be enabled via a thresholding method, wherein events of energy in a particular frequency band exceeding a given threshold trigger alarms which can be stored and listened to by an operator, and linked with any changes in the physical shape of the structure given by the position sensing embodiments described above.

Whilst the embodiments described above may be used with almost any structure, particular embodiments are directed at the case where the structure is a subsea riser, and hence below we consider several installation issues of installing the optic fiber DAS on risers of different types.

Installation Issues

The way in which the a DAS-based riser monitoring system is installed and applied will vary between riser types. Next, a brief discussion of each of the main types of risers is given along with a description of the way in which an optic fiber DAS can be used for that riser. It has been clearly stated where particular challenges arise as a result of the riser configuration. Note that these issues apply to the installation of the fiber generally, and hence to both the positioning and vibration detection embodiments.

Steel Catenary Riser (SCR)

Steel catenaries are a promising environment for testing of an optic fiber DAS, because fatigue monitoring is of critical importance in at least two zones. At the upper end of the riser, the complex loading conditions result in a need for detailed knowledge concerning the hang off angle and its variation in time. This will be particularly beneficial in the region of the touch down point, where there is a continuously varying riser angle which is not straightforward to evaluate using discrete sensors. The central portion of the water column, where the riser angle varies only slightly with depth, is a region that has not been widely observed with conventional monitoring technology. The application of an optic fiber DAS in accordance with embodiments of the invention will allow operators to have detailed information concerning the mode shapes along the entire length of these risers, as well as their relative amplitudes.

Top Tensioned Riser (TTR)

For a TTR, interface loads at the seabed and at the hull riser guide locations need monitoring. Usefully, the distributed monitoring system can provide information concerning riser tensioner stroke, fatigue cycles at the stress joints, and vortex induced vibration (VIV) information. The VIV monitoring would be performed in much the same manner as for SCRs.

Flexible Riser

Flexible risers offer an opportunity to capitalize on the key strengths for the acoustic positioning optic fiber DAS technology. Flexible risers facilitate greater vessel motion than the other risers described so far. In the case where multiple flexible risers emanate from a single vessel, the risers can be at risk of entanglement. Acoustic positioning can be useful for monitoring these situations in real time. Since flexible pipe exhibits very little bending stiffness, ocean currents can induce greater lateral motion than in the case of TTRs or SCRs. In the regions where flexible risers are forced to exhibit high bending radii, fatigue cycles are important to monitor. An optic fiber DAS of the present embodiments would be well suited to monitoring these types of risers, particularly where the fiber installation can be controlled at the time of the original riser deployment to ensure maximum riser/fiber cohesion.

Drilling Riser

Drilling risers are potentially a very good application for the monitoring technology of the described embodiments. The predictable geometry and potential proximity of the optical cable to the riser exterior are ideal for the acoustic positioning system capability. Further, the need for detailed VIV information during drilling means that the information generated by the system returns data which is of high value to the end user.

Hybrid Riser

Hybrid risers offer a geometry which is a combination of drilling and flexible risers. The capabilities from these two types of systems (above) can be combined in a hybrid installation. Thus the capabilities of the optic fiber DAS-based systems of the above described embodiments can be customized to ensure maximum value in both the flexible upper section and the stiff vertical section.

Installation Effects

As discussed above, there exists within subsea operations a variety of types of risers on which optic fiber DAS-based monitoring can be successfully implemented. In those cases where it is not possible to install a new fiber (e.g. n those cases where it is desired to retrofit the interferometer and processor to the end of an existing optical fiber), the installation of the pre-existing cable will affect the way in which the system operates. Two of the key issues affecting transduction, being cable insulation and cable clamping, are presented below.

It was mentioned earlier that cable insulation is an important factor in determining the acoustic sensitivity of a given cable. Insulation is however neither universally beneficial nor detrimental to cable sensitivity. In designing specialty acoustic transduction cables, some lightweight cable coatings can be helpful in reducing the impedance mismatch between a cable and its surroundings. This mechanical matching can allow some armored cables to exhibit unexpectedly high acoustic sensitivity. Generally, however, armored fiber optic cables which have not been specially designed with acoustic observation in mind are mediocre performers from an acoustic transduction standpoint. An additional type of 'insulation' arises from materials standing between the cable and the medium of interest. Consider for instance an umbilical contained within the cross-section of a riser. That umbilical will be acoustically obscured from the surroundings rendering it difficult to perform effective acoustic transduction. Therefore in order to maximize the signal-to-noise ratio for the acoustic positioning embodiments above, it is best to take advantage of cables which are in direct contact with the surroundings and specialized for acoustic observation.

With respect to effects arising from clamps, many risers feature cables which are clamped to the riser. These clamps can be present in a variety of forms, each of which will affect transduction. Since the acoustic energy of interest in the acoustic positioning embodiments is on the order of 10s of kilohertz and clamps are most generally made of dense metals at spacings on the order of 10s of meters, the clamps are not acoustically relevant. However, the vortex-induced-vibrations of interest for the vibration detection embodiments are at very low frequencies, and therefore consist of waves long enough to encompass many (or even many 10s of) clamps. These clamps are therefore relevant to the vibration detection embodiments.

Three main classes of clamps exist; continual clamps, where a line is contained within a groove; interior clamps, where spacers suspend the line within the riser cross-section; and exterior clamps, where the line is suspended outside the cross-section of the riser using clamps. For vibration monitoring, where the waves of interest are 100 m long or longer, the inter-clamp spacing is unimportant provided that the clamp structure is rigid and semi-regular. This is because the clamps are rigid from the perspective of waves much below 50 Hz, and they will therefore convey all of the information of interest. This is independent of whether the cable is suspended on the inside or the outside of the riser.

Various modifications, whether by way of addition, deletion or substitution may be made to the above described embodiment to provide further embodiments, any and all of which are intended to be encompassed by the appended claims.

REFERENCES

Fistas, N., & Manikas, A. (1994). A new general global array calibration method. *ICASSP Proceedings* (pp. 73-76). IEEE.

Kamil, Y. (2011). *Localisation and tracking in arrayed wireless sensor networks*. London: Theis (PhD), Department of Electrical and Electronic Engineering, Imperial College London.

Knudsen, V. O., Alford, R. S., & Emling, J. W. (1948). Underwater ambient noise. *Journal of Marine Research* (7), 410.

Kutlik, R., & Allen, J. (1998). Flow Assurance Instrumentation. *Offshore Technology Conference*, 8733-MS.

Mellen, R. H. (1952). Thermal-noise limit in the detection of underwater acoustic signals. *Journal of the Acoustical Society of America*, 24, 478.

Thorp, W. H. (1966). Analytic Description of the low frequency sound attenuation in the Deep Ocean. *Journal of the Acoustical Society of America*, 39 (904).

Urick, R. J. (1984). *Ambient noise in the sea*. Department of the Navy (US), Naval Sea Systems Command. 20070117128.

Urick, R. J. (1967). *Principles of underwater sound* (Vol. 3). Los Altos, Calif., USA: Peninsula Publishing.

Urick, R. (1983). *Principles of underwater sound*. McGraw-Hill.

The invention claimed is:

1. A method of resonant vibration detection in a subsea riser tethered at opposite ends and a portion thereof free to move therebetween, the method using an optical fiber distributed acoustic sensor (DAS) having an optical fiber, the optical fiber being coupled to the subsea riser at at least two points in the portion such that a known part of the optical fiber is adjacent to, connected to and moves with a known part of the portion of the subsea riser that is free to move, the method comprising:

detecting backscattered light on the fiber as it moves with the subsea riser, the backscatter being dependent on strain induced in the fiber due to mechanical strain in the subsea riser caused by resonant vibrations occurring in the subsea riser as the portion between the two tethered ends moves;

from the detected backscatter, processing a signal representative thereof to determine a frequency of oscillation of the resonant vibrations of the subsea riser as the portion between the two tethered ends moves; and frequency filtering the signal detected by the optical fiber DAS to obtain low frequencies, wherein the low frequencies are used for detecting the resonant vibrations of the subsea riser as the portion between the two tethered ends moves, wherein the low frequencies comprise frequencies of less than 50 Hz.

2. A method according to claim 1, wherein the low frequencies comprise frequencies of 1 Hz or less.

3. A method according to claim 1, and further comprising undertaking passive acoustic monitoring.

4. A method according to claim 3, wherein the passive acoustic monitoring comprises detecting acoustic events having an energy greater than a predetermined energy threshold.

5. A method according to claim 1, wherein the vibrations are due to mechanical vibrations rather than acoustic vibrations.

6. The method according to claim 1, wherein the low frequencies comprise frequencies of less than a few Hz.

7. A method according to claim 1, wherein the optical fiber is coupled to the subsea riser using a plurality of clamps at regular spaced intervals along the length of the optical fiber.

8. A method according to claim 1, wherein the optical fiber is coupled to the subsea riser using a plurality of clamps, wherein the fundamental mechanical resonance of the clamps is of a higher frequency than any resonant vibrations of the subsea riser.

9. A method according to claim 1, wherein the optical fiber is coupled to the subsea riser using a plurality of clamps, wherein the inter-clamp spacing is smaller than the wavelength of the resonant vibrations.

10. A system for detecting the resonant vibrations of a subsea riser tethered at opposite ends and a portion thereof free to move therebetween, the system comprising:
an optical fiber distributed acoustic sensor (DAS) system having an optical fiber, the optical fiber being coupled to the subsea riser at at least two points in the portion such that a known part of the optical fiber is adjacent to, connected to and moves with a known part of the portion of the subsea riser that is free to move, the sensor system further comprising:
an interferometer arrangement arranged to detect backscattered light on the fiber as it moves with the subsea riser, the backscatter being dependent on strain induced in the fiber due to mechanical strain in the subsea riser caused by resonant vibrations occurring in the subsea riser as the portion between the two tethered ends moves; and
a processor arranged, from the detected backscatter, to process a signal representative thereof to determine a frequency of oscillation of the resonant vibrations of the subsea riser as the portion between the two tethered ends moves,
wherein the processor is further arranged to frequency filter the signal detected by the optical fibre DAS to determine low frequencies, wherein the low frequencies are used for detecting the resonant vibrations of the subsea riser as the portion between the two tethered ends move,
wherein the low frequencies are frequencies less than 50 Hz.

11. A system according to claim 10, wherein the low frequencies are frequencies of 1 Hz or less.

12. A system according to claim 10, wherein the processor is further arranged to undertake passive acoustic monitoring.

13. A system according to claim 12, wherein the passive acoustic monitoring comprises detecting acoustic events having an energy greater than a predetermined energy threshold.

14. A system according to claim 10, wherein the vibrations are caused by mechanical vibration rather than acoustic vibration.

15. The system according to claim 10, wherein the low frequencies are frequencies less than a few Hz.

16. A system according to claim 10, wherein the optical fiber is coupled to the subsea riser using a plurality of clamps at regular spaced intervals along the length of the optical fiber.

17. A system according to claim 10, wherein the optical fiber is coupled to the subsea riser using a plurality of clamps, wherein the fundamental mechanical resonance of the clamps is of a higher frequency than any resonant vibrations of the subsea riser.

18. A system according to claim 10, wherein the optical fiber is coupled to the subsea riser using a plurality of clamps, wherein the inter-clamp spacing is smaller than the wavelength of the resonant vibrations.

* * * * *